US012690788B2

(12) United States Patent
Hahn et al.

(10) Patent No.: US 12,690,788 B2
(45) Date of Patent: Jul. 28, 2026

(54) SMART CONTACT LENS FOR ULTRASENSITIVE DIABETES DIAGNOSIS

(71) Applicants: PHI BIOMED INC., Seoul (KR); POSTECH RESEARCH AND BUSINESS DEVELOPMENT FOUNDATION, Gyeongsangbuk-do (KR)

(72) Inventors: Sei Kwang Hahn, Seoul (KR); Su Kyoung Kim, Gyeongsangbuk-do (KR); Sang Baie Shin, Seoul (KR); Geon Hui Lee, Ulsan (KR); Hye Hyeon Han, Gyeongsangbuk-do (KR); Tae Yeon Kim, Gyeongsangbuk-do (KR)

(73) Assignees: PHI BIOMED INC. (KR); POSTECH RESEARCH AND BUSINESS DEVELOPMENT FOUNDATION (KR)

( * ) Notice: Subject to any disclaimer, the term of this patent is extended or adjusted under 35 U.S.C. 154(b) by 344 days.

(21) Appl. No.: 18/107,971

(22) Filed: Feb. 9, 2023

(65) Prior Publication Data

US 2024/0268723 A1 Aug. 15, 2024

(51) Int. Cl.
A61B 5/145 (2006.01)
A61B 5/00 (2006.01)
A61B 5/1486 (2006.01)

(52) U.S. Cl.
CPC ........ A61B 5/14865 (2013.01); A61B 5/0015 (2013.01); A61B 5/14507 (2013.01);
(Continued)

(58) Field of Classification Search
CPC ...... A61B 2560/045; A61B 2560/0468; A61B 2562/02; A61B 2562/125;
(Continued)

(56) References Cited

U.S. PATENT DOCUMENTS

| | | | | |
|---|---|---|---|---|
| 8,922,366 | B1 * | 12/2014 | Honore | G02C 11/10 |
| | | | | 351/158 |
| 9,861,710 | B1 * | 1/2018 | Ruckh | A61B 5/05 |

(Continued)

FOREIGN PATENT DOCUMENTS

| | | | | |
|---|---|---|---|---|
| CN | 112710713 B | * | 4/2022 | G01N 27/308 |
| KR | 20190020405 A | | 3/2019 | |

(Continued)

OTHER PUBLICATIONS

Zhai, Dongyuan, et al. "Highly sensitive glucose sensor based on Pt nanoparticle/polyaniline hydrogel heterostructures." ACS nano 7.4 (2013): 3540-3546.*

(Continued)

*Primary Examiner* — Eric J Messersmith
(74) *Attorney, Agent, or Firm* — Myers Bigel, P.A.

(57) ABSTRACT

The present disclosure relates to a smart contact lens for diabetes diagnosis in which a diabetic diagnosis sensor is composed of platinum-plated electrodes, and a driving system using the same.

The smart contact lens of the present disclosure is easy to mass-produce, has good wireless power transfer efficiency due to high electrical conductivity, may perform good communication with an external driving board, and may perform physically and electrochemically stable driving.

9 Claims, 16 Drawing Sheets

(52) U.S. Cl.
CPC ........ *A61B 5/14532* (2013.01); *A61B 5/6821* (2013.01); *A61B 2560/045* (2013.01); *A61B 2560/0468* (2013.01); *A61B 2562/02* (2013.01); *A61B 2562/125* (2013.01); *A61B 2562/164* (2013.01)

(58) Field of Classification Search
CPC ............ A61B 2562/164; A61B 5/0015; A61B 5/14507; A61B 5/14532; A61B 5/14865; A61B 5/6821; A61B 5/1486
See application file for complete search history.

(56) References Cited

U.S. PATENT DOCUMENTS

| | | | | |
|---|---|---|---|---|
| 2004/0045879 A1* | 3/2004 | Shults | .................... | C12Q 1/006 |
| | | | | 422/68.1 |
| 2007/0235331 A1* | 10/2007 | Simpson | .................. | A61B 5/00 |
| | | | | 204/403.01 |
| 2008/0135408 A1* | 6/2008 | Sjolander | ............. | A61B 5/1468 |
| | | | | 204/403.01 |
| 2009/0084678 A1* | 4/2009 | Joshi | .................. | A61B 5/14865 |
| | | | | 204/403.14 |
| 2016/0100778 A1* | 4/2016 | Yi | ........................ | A61B 5/6833 |
| | | | | 600/345 |
| 2020/0070403 A1* | 3/2020 | Yi | .......................... | C12Q 1/006 |

FOREIGN PATENT DOCUMENTS

| | | |
|---|---|---|
| KR | 20200069006 A | 6/2020 |
| KR | 20210028958 A | 3/2021 |
| KR | 20210094481 A | 7/2021 |
| KR | 20220148746 A | 11/2022 |

OTHER PUBLICATIONS

Kellon, Jaclyn E., Samantha L. Young, and James E. Hutchison. "Engineering the nanoparticle-electrode interface." Chemistry of Materials 31.8 (2019): 2685-2701.*

Lipinska, Wiktoria, Katarzyna Grochowska, and Katarzyna Siuzdak. "Enzyme immobilization on gold nanoparticles for electrochemical glucose biosensors." Nanomaterials 11.5 (2021): 1156.*

Fritea, Luminita, et al. "Metal nanoparticles and carbon-based nanomaterials for improved performances of electrochemical (Bio) sensors with biomedical applications." Materials 14.21 (2021): 6319.*

Hassan, Mohamed H., et al. "Recent advances in enzymatic and non-enzymatic electrochemical glucose sensing." Sensors 21.14 (2021): 4672.*

Dayakar Thatikayala, "Progress of Advanced Nanomaterials in the Non-Enzymatic Electrochemical Sensing of Glucose and H2O2", from Biosensors 2020, 10, 151, pp. 1-34.

* cited by examiner

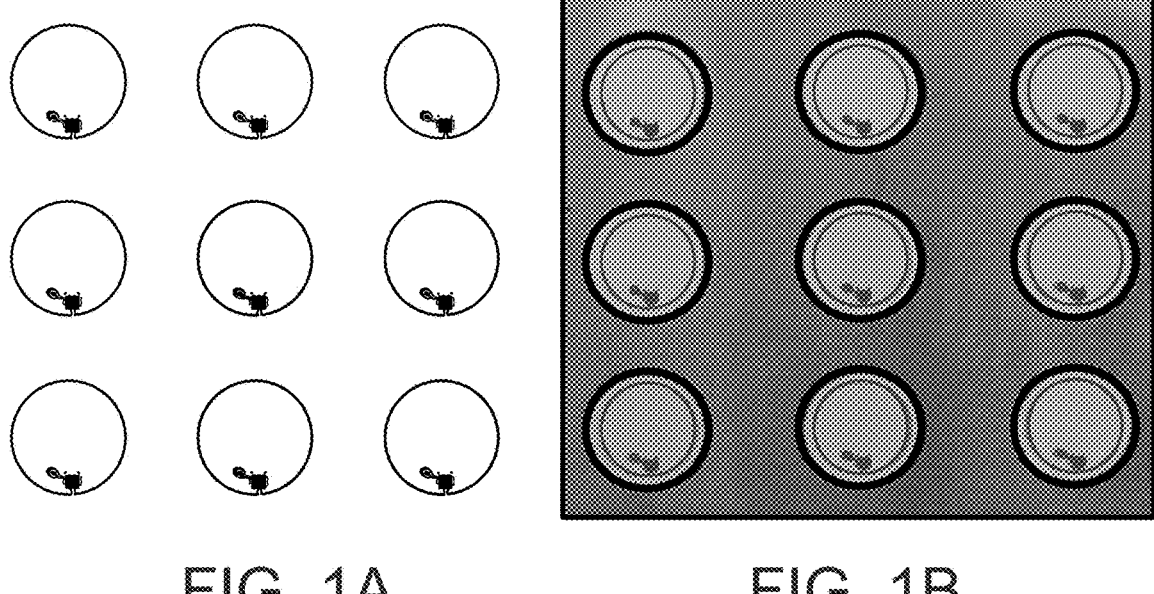
FIG. 1A
FIG. 1B
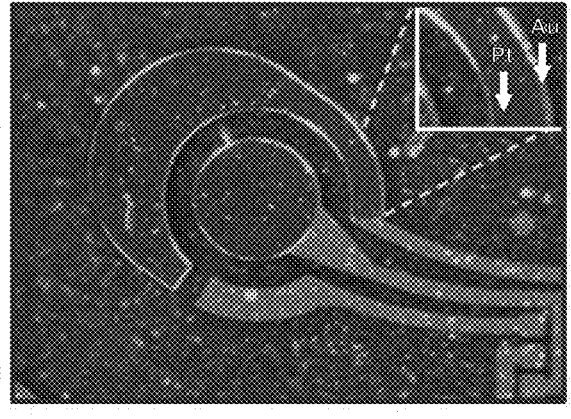
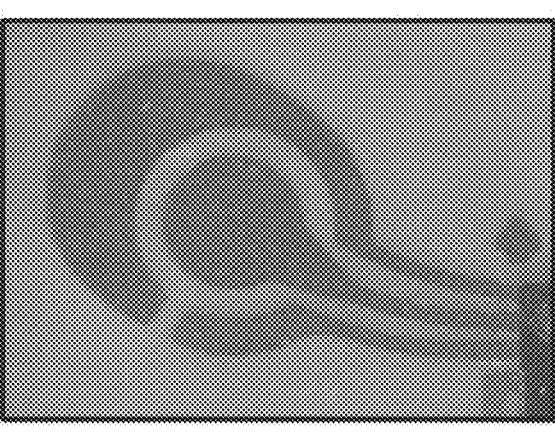
FIG. 2A
FIG. 2B

50μm

| Element | Line Type | Wt% | Wt% Sigma | Atomic % |
|---|---|---|---|---|
| Ni | K series | 0.00 | 0.10 | 0.00 |
| Cu | L series | 0.67 | 0.14 | 2.02 |
| Ag | L series | 0.00 | 0.11 | 0.00 |
| Pt | M series | 99.33 | 0.14 | 97.98 |
| Au | M series | 0.00 | 0.32 | 0.00 |
| Total: | | 100.00 | | 100.00 |

FIG. 3C

| Substrate Type | | | | | |
|---|---|---|---|---|---|
| Deposition 300 nm | | | | | |
| Deposition 500 nm | | | | | |
| Deposition 700 nm | | | | | |
| Pt Plated | | | | | |
| | 0.1 | 0.5 | 1 | 2 | 3 |

Distance (cm)

Wireless power & Communication

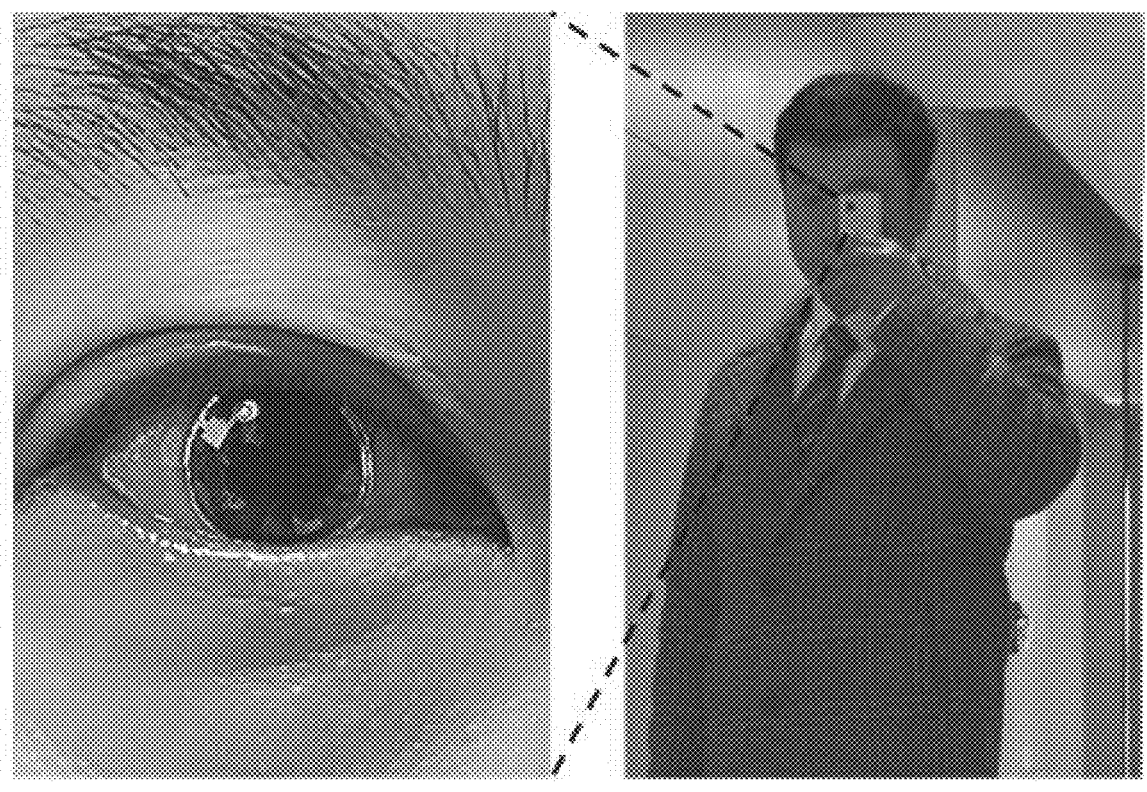
FIG. 12A                              FIG. 12B

Wireless power & Communication

SMART CONTACT LENS FOR ULTRASENSITIVE DIABETES DIAGNOSIS

BACKGROUND

1. Field of the Invention

The present disclosure relates to a smart contact lens for ultrasensitive diabetes diagnosis in which a diabetes diagnosis sensor is composed of platinum-plated electrodes which is useful for mass production and has improved electrical conductivity, physical stability, and electrochemical stability, and a driving system thereof.

The present disclosure was made with the support of the Ministry of Science and ICT(MSIT) under the project identification number 1711159537 and the project number 2021M3E5E7021473, and the research management professional organization for the project is the National Research Foundation of Korea, the research program name is "Disease-focused translational research program," the research project name is "Smart contact lens for diagnosis and treatment of diabetic retinopathy," the host organization is Pohang University of Science and Technology, and the research period is from Jan. 1, 2022 to Dec. 31, 2022.

Further, the present disclosure was made with the support of the MSIT under the project identification number 1711154265 and the project number 2020R1A2C3014070, and the research management professional organization for the project is the National Research Foundation of Korea, the research program name is "Personal basic research," the research project name is "Development of diabetes diagnosis and an optogenetic treatment system using multifunctional nanomaterials," the host organization is Pohang University of Science and Technology, and the research period is from Mar. 1, 2022 to Feb. 28, 2023.

In addition, the present disclosure was made with the support of the MSIT under the project identification number 1711175310 and the project number 2022M3C1C3095052, and the research management professional organization for the project is the National Research Foundation of Korea, the research program name is "STEAM research," the research project name is "Development of a smart contact lens for optical diagnosis and treatment of diabetes," the host organization is Pohang University of Science and Technology, and the research period is from Sep. 1, 2022 to Feb. 28, 2023.

2. Discussion of Related Art

Recently, due to the explosive increase in diabetic patients worldwide, related medical expenses are rising, and the prevalence of complications due to the increase in diabetic patients is also increasing. Nevertheless, self-diabetes management rates of the diabetic patients are generally low, and compliance with self-monitoring of blood glucose or the like is also low. In order to prevent life-threatening hyperglycemia and hypoglycemia in diabetic patients, it is important to maintain a target blood glucose level by measuring blood glucose three or more times a day.

The most common method of self-measuring blood glucose is a blood glucose test by drawing blood from a finger, and since considerable pain accompanies due to pain-sensing cells and nerve tissue distributed in large quantities in the finger, patients repeatedly experience pain during each drawing of blood. Further, problems such as secondary infections due to inappropriate disinfection, injection waste can be caused.

Recently, continuous glucose monitoring systems (CGMs), which can continuously measure blood glucose from interstitial fluid by subcutaneous insertion of a microneedle into a patient's body and perform monitoring in conjunction with a smartphone, have been developed and are in the spotlight as a replacement for a blood glucose meter, but there is a limitation in universal application due to problems such as body hair, skin redness, and the like, discomfort during outdoor activities or exercise due to continuous wearing, and high costs. Further, there is a problem such as reduced oxygen diffusion due to contamination of the sensor and inflammation in the skin.

In order to solve these problems, the technology of a smart contact lens, which is a next-generation wearable device, is a technology that many companies around the world are competing to develop. The smart contact lens is a device capable of applying technologies such as continuous blood glucose measurement, optical treatment, intraocular pressure measurement, electronically controlled drug administration, and the like. In order to solve the problem of the continuous blood glucose meter, a highly sensitive contact lens-type continuous blood glucose meter including a nanocatalyst has been developed, but in consideration of instability, conductivity, and productivity of a thin film due to an electrochemical reaction, there are areas to be improved in terms of materials and structure. Further, when an organic solvent is used in a process of forming and cleaning the electrodes of a sensor, problems such as a change in shape of the contact lens and separation of the electrodes due to a swelling phenomenon of silicone hydrogel are still present.

In addition, a portable wireless controller for driving of a smart contact lens for diabetes diagnosis is required. Wireless power is converted to a radio frequency (RF) signal having a specific frequency from a transmitter circuit of the controller and transmitted to an antenna. In this case, a generated magnetic field can be induced to the antenna of the smart contact lens to transmit electromagnetic wave energy. Further, as a load linked to a sensor of various functions in the smart contact lens is changed, a change in impedance of the controller antenna can be sensed to sense a sensor signal in the contact lens. As described above, the wireless controller can sense wireless power supply and the sensor signal for driving the smart contact lens. Further, the wireless controller can be connected to the smart device to perform functions such as real-time monitoring of the sensor signal of the smart contact lens, wireless control, sensor control, and the like.

SUMMARY OF THE INVENTION

The present disclosure is directed to developing a smart contact lens system for diabetes diagnosis which is easy to mass-produce, has good wireless power transfer efficiency due to high electrical conductivity, can perform good communication with an external driving board, and can perform physically and electrochemically stable driving.

Further, the present disclosure is directed to providing a portable wireless controller having functions such as sufficient wireless power supply, wireless control, sensor data sensing, and the like to drive a smart contact lens for diabetes diagnosis.

In addition, the present disclosure is directed to providing a portable wireless controller capable of monitoring sensed sensor data of a smart contact lens for diabetes diagnosis in real time, collecting data, and controlling a function change and the like using a smartphone.

The present disclosure provides a smart contact lens for diabetes diagnosis including: a platinum-plated electrode including an electrically conductive layer and a reaction layer; and a porous hydrogel including a nanocatalyst, wherein the reaction layer includes platinum (Pt).

Further, the present disclosure provides a method of manufacturing the above-described smart contact lens for diabetes diagnosis, including: (S1) forming three electrodes (a working electrode, a counter electrode, and a reference electrode) and an antenna on a flexible substrate; (S2) insulating the flexible substrate after attaching a polydimethylsiloxane (PDMS) film on the three electrodes and the antenna; (S3) putting the flexible substrate in a mold for manufacturing a lens and crosslinking the flexible substrate to manufacture a contact lens; (S4) opening a three-electrode region in a contact lens and removing the PDMS film to expose the three-electrode region; and (S5) coating a porous hydrogel including a nanocatalyst on the working electrode, wherein one or more of the working electrode and the counter electrode are a platinum-plated electrode.

Further, the present disclosure provides a driving system including: the above-described smart contact lens for diabetes diagnosis; and a wireless controller for driving the smart contact lens for diabetes diagnosis.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which:

FIG. 1A illustrates a board design diagram of a smart contact lens for diabetes diagnosis according to the present disclosure and FIG. 1B illustrates a board design diagram of a smart contact lens for diabetes diagnosis according to the present disclosure;

FIG. 2A illustrates a sensor electrode of a gold/platinum thin film manufactured in Comparative-Manufacturing Example 1; FIG. 2B illustrates a sensor electrode of a platinum-plated electrode manufactured in Manufacturing Example 1;

FIG. 3C is an energy dispersion spectroscopy result of a platinum-plated electrode according to the present disclosure;

FIG. 12A illustrates a smart contact lens according to the present disclosure in a human eye as explained in Experimental Example 4. FIG. 12B shows a wireless controller according to the present disclosure held to the human eye as explained in Experimental Example 4.

DETAILED DESCRIPTION OF EXEMPLARY EMBODIMENTS

Figure 3A:
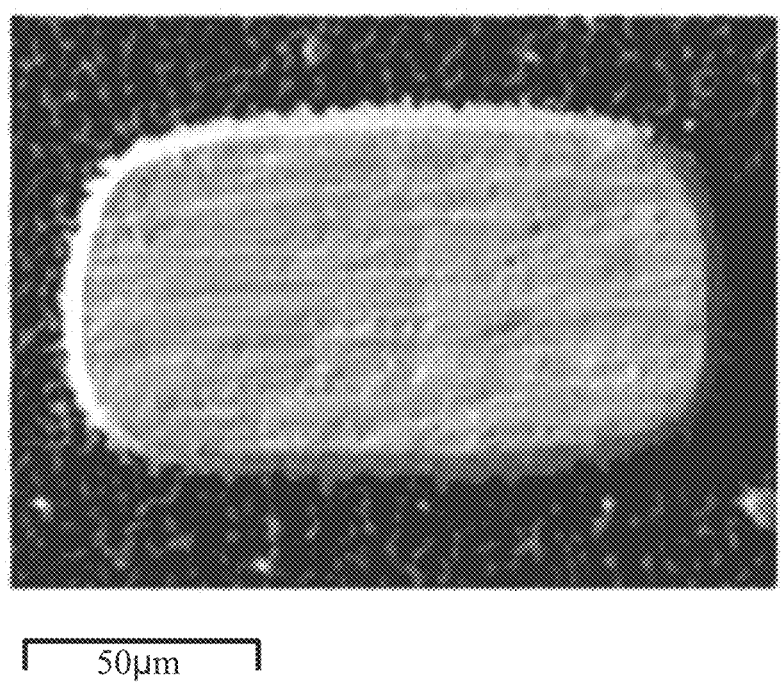
FIG. 3A illustrates a scanning electron microscope image of a platinum-plated electrode according to the present disclosure.

Hereinafter, the present disclosure will be described in more detail.

A smart contact lens for diabetes diagnosis according to the present disclosure is useful for mass production and can detect glucose in tears with high sensitivity and accuracy. Accordingly, the smart contact lens for diabetes diagnosis can be expressed as a smart contact lens for ultrasensitive diabetes diagnosis.

The contact lens of the present disclosure may be based on one or more selected from the group consisting of a silicone elastomer, silicone hydrogel, polydimethyloxane (PDMS), poly(2-hydroxyethylmethacrylate) (PHEMA), and polyethylene glycol methacrylate (PEGMA).

In one embodiment, the silicone hydrogel may include one or more hydrophilic monomers such as 2-hydroxyethyl methacrylate (HEMA), n-vinyl pyrrolidone (NVP), dimethylacrylamide (DMA) and methacrylic acid (MAA), and may further include a crosslinker, an ultraviolet (UV) light absorber, and the like.

In the present disclosure, the smart contact lens for diabetes diagnosis includes a glucose sensor therein, and the glucose sensor includes a platinum-plated electrode, and a porous hydrogel including a nanocatalyst.

In the present disclosure, the platinum-plated electrode has a structure in which platinum is formed by plating, specifically electroless plating, in a flexible substrate. In comparison with a conventionally used electrode, this platinum-plated electrode may prevent electrode damage, and side effects and side reactions due to ionic actions which may occur during an electrochemical reaction in tears or physiological saline.

In one embodiment, the platinum-plated electrode may be used as one or more of a working electrode and a counter electrode.

In one embodiment, the platinum-plated electrode may include an electrically conductive layer and a reaction layer.

In one embodiment, the electrically conductive layer may include copper. The copper may improve the physical stability of platinum plating used for the working electrode and the counter electrode.

In one embodiment, an intermediate layer may be formed between the electrically conductive layer and the reaction layer. This intermediate layer may include ruthenium and/or nickel. In the present disclosure, the plating of platinum as a reaction layer may be performed in a region where the intermediate layer is formed.

In one embodiment, the reaction layer is the uppermost layer of the electrode, and an electrochemical reaction is performed in the reaction layer. The reaction layer may be composed of a metal capable of promoting an electrochemical reaction, and platinum may be used as such a metal.

In one embodiment, the thickness of the electrically conductive layer in the entire platinum-plated electrode may be 70 to 98%, 73 to 97%, or 90 to 98% of the total thickness of the electrode.

In one embodiment, the platinum-plated electrode may have a structure of platinum (Pt)/ruthenium (Ru)/copper (Cu) or platinum/nickel (Ni)/gold (Au)/nickel/copper.

In one embodiment, the thickness of the platinum-plated electrode is not particularly limited as long as it is applicable to a contact lens, and may be 0.1 to 10 μm.

In the present disclosure, the platinum-plated electrode may be formed on a flexible substrate through an electroless plating process to be used as an electrode of a wearable device such as a smart contact lens or the like.

In one embodiment, the flexible substrate may be one or more selected from the group consisting of polyimide (PI), colorless PI (CPI), polyethylene naphthalate (PEN), and polycarbonate (PC). In the present disclosure, the PI or CPI may be used as the flexible substrate. The PI or CPI has excellent thermal resistance, and thus may be applied to a plating process. However, when cutting with a laser cutter in a manufacturing process of contact lenses, since residual carbonized portions are generated, the PI or CPI may not be used as a substrate that is inserted into a contact lens. In the present disclosure, as the CPI is cut using a press cutter, the corresponding material may be applied as the flexible substrate.

The thickness of the flexible substrate is not particularly limited as long as it is applicable to the smart contact lens, and may be 1 to 100 μm.

In one embodiment, the flexible substrate may be a substrate surface-treated with UV-Ozone, $O_2$ plasma, and an organic material. One or more functional groups selected from the group consisting of a carboxyl group, an alcohol group, a thiol group, an amine group, and an aldehyde group may be formed on the flexible substrate by the surface treatment.

In one embodiment, the platinum-plated electrode may be an electrode surface-treated with a first biocompatible polymer. Unnecessary current generation may be prevented and electrochemical stability of the electrode in an electrolyte may be increased by the surface treatment. In the present disclosure, the surface treatment may be expressed as "coating."

The type of first biocompatible polymer is not specifically limited, and may be one or more selected from the group consisting of polyethylene glycol, polylactic acid, polyglycolic acid, polylactic-co-glycolic acid, polyvinylpyrrolidone, hyaluronic acid (HA), and a derivative thereof.

The first biocompatible polymer includes a functional group at an end or a branch of the structure, and this functional group may be selected from among a thiol group (—SH), an amine group (—NH$_2$), a carboxyl group (—COOH), and a hydroxyl group (—OH). The first biocompatible polymer may form a chemical bond with the reaction layer of the platinum-plated electrode by the functional group. Specifically, the first biocompatible polymer may form one or more bonds selected from the group consisting of a gold-thiol bond, an amide bond, an ester bond, and a dithiol bond with the reaction layer.

The molecular weight of the first biocompatible polymer may be 1 to 1000 kDa, or 5 to 200 kDa.

In the present disclosure, a defect such as dissolution in an electrolyte solution may be minimized by using hyaluronic acid (HA) as the first biocompatible polymer. Since the hyaluronic acid has high biocompatibility and a strong negative charge, the lifespan of the electrode may be increased by effectively defending against the approach of negative ions, which cause metal corrosion in the electrolyte.

In the present disclosure, the platinum-plated electrode may be manufactured through transferring an electrically conductive layer onto the flexible substrate, plating an intermediate layer on the electrically conductive layer, plating a reaction layer on the intermediate layer, and surface-treating the reaction layer with a first biocompatible polymer.

In one embodiment, detailed descriptions of the flexible substrate, the electrically conductive layer, the intermediate layer, the reaction layer, and the first biocompatible polymer are the same as described above.

In one embodiment, a case in which hyaluronic acid (HA) is used as a first biocompatible polymer may be expressed as a hyaluronic acid (HA)-platinum-plated electrode.

The smart contact lens for diabetes diagnosis of the present disclosure includes a porous hydrogel including a nanocatalyst together with the above-described platinum-plated electrode.

In one embodiment, the nanocatalyst may include one or more metals selected from the group consisting of gold and platinum.

In one embodiment, the nanocatalyst may be gold nanoparticles. Further, the nanocatalyst may be a bimetallic nanocatalyst including two metals.

The bimetallic nanocatalyst may maximize catalytic activity by adjusting the electronic level of the main metal through a combination of two metals (the main metal and sub-metal). Accordingly, the sensitivity and reaction rate of glucose measurement may be improved.

The weight ratio of each of the two metals may be 30 to 70 weight %, and a metal having a high weight ratio may be referred to as the main metal.

In one embodiment, the bimetallic nanocatalyst may be prepared through a seed-mediated growth method in which the sub-metal is grown based on the main metal. Further, the bimetallic nanocatalyst may have a core-shell structure or an alloy structure.

In one embodiment, the nanocatalyst may improve the sensitivity for a substance to be measured in a body fluid, and in this case, the substance to be measured may be selected from glucose, galactose, cholesterol, lactic acid, and hydrogen peroxide.

In one embodiment, the nanocatalyst may be surface-treated with a second biocompatible polymer. The dispersibility of the nanocatalyst and fixing force in the hydrogel may be increased by the surface treatment.

The type of second biocompatible polymer is not specifically limited, and may be one or more selected from the group consisting of polyethylene glycol, polylactic acid, polyglycolic acid, polylactic-co-glycolic acid, polyvinylpyrrolidone, hyaluronic acid, and a derivative thereof.

The second biocompatible polymer includes a functional group at an end or a branch of the structure, and this functional group may be selected from among a thiol group (—SH), an amine group (—NH$_2$), a carboxyl group (—COOH), and a hydroxyl group (—OH). The second biocompatible polymer may be chemically bonded with a surface of the nanocatalyst by the functional group, and the strength of the chemical bond may be adjusted by adjusting a substitution rate of the functional group. The chemical bond may be selected from among a gold-thiol bond, an amide bond, and an amine bond.

The molecular weight of the second biocompatible polymer may be 1 to 1000 kDa, or 5 to 200 kDa.

In one embodiment, when the bimetallic nanocatalyst is prepared using a seed-mediated growth method (the main metal is Au, and the sub-metal is Pt), the prepared bimetallic nanocatalyst may be expressed as a gold@platinum bimetallic nanocatalyst. Further, a case in which hyaluronic acid (HA) is used as a second biocompatible polymer may be expressed as a hyaluronic acid (HA)-gold@platinum bimetallic nanocatalyst.

In the present disclosure, the nanocatalyst is included in the porous hydrogel. The porous hydrogel may improve the reliability and stability of long-term glucose measurement to allow ultra-sensitive diabetes diagnosis.

In one embodiment, the porous hydrogel may be composed of a third biocompatible polymer having hydrophilicity.

The third biocompatible polymer may have a molecular weight of 1 to 200 kDa.

The type of third biocompatible polymer is not specifically limited, and may be one or more selected from the group consisting of polyvinyl alcohol (PVA), chitosan, and hyaluronic acid (HA). In the present disclosure, polyvinyl alcohol and chitosan may be used together.

In one embodiment, the porous hydrogel may further include glucose oxidase (GOx).

In one embodiment, the porous hydrogel may be prepared through crosslinking a solution including the nanocatalyst, the glucose oxidase (GOx), the third biocompatible polymer, and magnesium particles, and removing the magnesium particles.

Detailed descriptions of the nanocatalyst, the glucose oxidase, and the third biocompatible polymer are the same as described above.

In one embodiment, the content of the nanocatalyst may be 0 to 5 vol % based on the total amount of the solution.

When polyvinyl alcohol and chitosan are used as the third biocompatible polymer, a 0 to 10 wt % polyvinyl alcohol solution may be used, and a 0 to 1 wt % chitosan solution may be used.

In one embodiment, the magnesium particles may be used to prepare a porous structure, and as the magnesium particles, nano-sized or micro-sized particles may be used depending on the size of the porous structure, and specifically, particles having sizes of 200 to 500 nm may be used. The decomposition rate of the magnesium particles may vary depending on pH.

These magnesium particles may be converted to magnesium hydroxide particles by reacting with water (H$_2$O), and the magnesium hydroxide particles may form a porous structure in the hydrogel while being dissociated into magnesium ions by reacting with cations (Ca$^{2+}$, K$^+$, Na$^+$, and the like).

In one embodiment, the content of the magnesium particles may be 0 to 100 mg/ml based on the total amount of the solution.

In one embodiment, in crosslinking, a method of drop-casting and drying a solution including the nanocatalyst, the glucose oxidase, the third biocompatible polymer, and the magnesium particles, and then drop-casting and crosslinking a solution including a crosslinker may be used.

In this case, a crosslinker commonly used in the art, such as glutaraldehyde or the like, may be used as the crosslinker.

In one embodiment, the removal of the magnesium particles may be performed by immersing a crosslinked crosslinking material in a solvent, and phosphate buffered saline (PBS) having a pH of 5 to 10 and an aqueous solution including the above cations may be used as the solvent.

In one embodiment, after preparing the porous hydrogel, in order to remove unreacted substances, a process of cleaning the hydrogel for 2 to 24 hours by immersing the hydrogel in 1× phosphate buffered saline (PBS) of pH 5 to 8 may be further included.

In one embodiment, the porous hydrogel including the nanocatalyst may be coated on the working electrode of an electrochemical glucose sensor.

In the present disclosure, an antenna may be formed on the flexible substrate of the smart contact lens. The antenna may transmit and receive power and signals to and from the outside through induced current and electromagnetic resonance.

The antenna may be formed on the same surface as the sensor on the flexible substrate.

In one embodiment, the antenna may be a circular antenna having a circular structure.

In one embodiment, the antenna may be composed of a nanomaterial, and the nanomaterial may include one or more selected from the group consisting of a zero-dimensional material which is a nanoparticle, a one-dimensional nanomaterial which is a nanowire, a nanofiber, or a nanotube, and a two-dimensional nanomaterial which is graphene, MoS$_2$, or a nanoflake.

In one embodiment, the antenna may be a platinum-plated antenna. In the present disclosure, both the electrode and the antenna may be formed by platinum plating, but each may serve as an electrode and an antenna through differences in the shape of a pattern, thicknesses of the electrically conductive layer to be plated and the reaction layer including platinum, and the like.

Further, in the present disclosure, an application-specific integrated circuit (ASIC) chip and the like may be formed on the flexible substrate.

Further, the present disclosure relates to a method of manufacturing the above-described smart contact lens for diabetes diagnosis.

The smart contact lens for diabetes diagnosis of the present disclosure may include (S1) forming three electrodes (a working electrode, a counter electrode, and a reference electrode) and an antenna on a flexible substrate, (S2)

insulating the flexible substrate after attaching a polydim-ethylsiloxane (PDMS) film on the three electrodes and the antenna, (S3) putting the flexible substrate in a mold for manufacturing a lens and crosslinking the flexible substrate to manufacture a contact lens, (S4) removing the PDMS film to expose a three-electrode region after opening the three-electrode region in the contact lens, and (S5) coating a porous hydrogel including a nanocatalyst on the working electrode.

In the present disclosure, operation S1 is a process of forming the three electrodes (a working electrode, a counter electrode, and a reference electrode) and the antenna on the flexible substrate.

In one embodiment, descriptions of the flexible substrate are the same as described above.

In the present disclosure, one or more of the working electrode and the counter electrode may be a platinum-plated electrode. Further, the antenna is a platinum-plated antenna, and may be formed by platinum plating. Descriptions of the platinum-plated electrode and the platinum-plated antenna are the same as described above, and the platinum-plated electrode and the platinum-plated antenna may each serve as an electrode and an antenna through differences in the shape of a pattern, thicknesses of an electrically conductive layer to be plated and a reaction layer, and the like.

In one embodiment, the reference electrode may be composed of a silver/silver chloride (Ag/AgCl) thin film and a paste.

In one embodiment, the area of the working electrode may be 0.1 to 2 mm$^2$.

In one embodiment, the shape of the electrode is not specifically limited, and may include, for example, a circular shape, a quadrangular shape, and the like.

In one embodiment, an application-specific integrated circuit (ASIC) chip for glucose measurement and control of the smart contact lens may be additionally formed on the flexible substrate. The ASIC chip may be formed by flip chip bonding.

In one embodiment, after forming the three electrodes, the antenna, and the ASIC chip on the flexible substrate, a process of cutting the remaining region of the flexible substrate with a press cutter may be additionally performed.

In the present disclosure, operation S2 is a process of insulating the flexible substrate after attaching the PDMS film on the three electrodes and the antenna. In this operation, the physical and electrochemical stability of the electrode may be increased by insulating a reaction portion of the electrode, that is, a region other than the three electrodes and a wire connection portion.

In one embodiment, in order to prevent insulation treatment of the three-electrode, a polydimethylsiloxane (PDMS) film may be attached after coating the surface of the three-electrode with a solution including PVA and glycerol.

The molecular weight of the PVA may be 1,000 to 10,000 g/mol, and the content of glycerol may be 0 to 10 wt %. Further, the PDMS film may be prepared by setting a ratio of a precursor and a crosslinker to 10:1, 15:1 or 20:1, and the PDMS film may have a thickness of 0.5 to 2 μm.

In one embodiment, the insulation treatment may be performed by coating one or more selected from the group consisting of a parylene-based polymer, polyurethane, epoxy, polydimethylsiloxane, and a silicone elastomer. Specifically, the insulation treatment may be performed by depositing a parylene-based polymer at a low temperature or coating an epoxy-based polymer and/or a silicon-based polymer.

A parylene-C polymer, a parylene-D polymer, a parylene-N polymer, a parylene-F polymer, or the like may be used as the parylene-based polymer.

In the present disclosure, an operation of performing O$_2$ plasma or UV ozone treatment after performing the insulation treatment to remove contaminants from the electrode surface and modifying the electrode surface to a hydrophile property may be further included.

In one embodiment, the UV treatment may be performed for 10 to 20 minutes using a UV cleaner.

In one embodiment, the ozone plasma treatment may be performed for 20 to 40 seconds or for 30 seconds at a power of 100 under a vacuum and oxygen atmosphere of $3 \times 10^{-6}$ torr or less using reactive ion etching (RIE) equipment (SNTEK BSC5004).

In the present disclosure, operation S3 is a process of putting the flexible substrate in the mold for manufacturing the lens and crosslinking the flexible substrate to manufacture the contact lens.

In one embodiment, the contact lens of the present disclosure may be based on one or more selected from the group consisting of a silicone elastomer, silicone hydrogel, polydimethyloxane (PDMS), poly(2-hydroxyethylmethacrylate) (PHEMA), and polyethylene glycol methacrylate (PEGMA).

In one embodiment, a solution for manufacturing the smart contact lens (a contact lens manufacturing solution) may include a silicone elastomer-based precursor and a crosslinker. The ratio of the precursor and the crosslinker may be 10:1 to 1:10.

In one embodiment, a smart contact lens including a flexible substrate having a platinum-plated electrode formed therein may be manufactured by the above operations.

In the present disclosure, operation S4 is a process of removing the PDMS film to expose the three-electrode region after opening the three-electrode region in the contact lens.

In the above operation, the glucose in the body fluid may be brought into contact with the electrodes of the electrochemical sensor, that is, the three electrodes, by cutting the region to which the PDMS film is attached with a circular punch and removing an upper surface of the sensor.

In the present disclosure, operation S5 is a process of coating the porous hydrogel including the nanocatalyst on the working electrode.

In one embodiment, the porous hydrogel may be coated after activating the surface of the working electrode with UV-Ozone or O$_2$ plasma.

In one embodiment, after applying a solution including the nanocatalyst, the glucose oxidase, the third biocompatible polymer, and the magnesium particles on the working electrode, completely drying the solution, and then applying and drying a crosslinking solution, the porous hydrogel may be coated by removing the magnesium particles with an organic solvent.

In one embodiment, the unreacted substances and organic solvent may be removed by coating the porous hydrogel and then immersing the resultant in PBS.

The smart contact lens for diabetes diagnosis according to the present disclosure is a wearable device including an electrochemical glucose sensor.

In one embodiment, an electrochemical sensor system may be formed using platinum-plated electrodes on a flexible substrate as a counter electrode and a working electrode, and using Ag/AgCl as a reference electrode. Further, as the working electrode of the electrochemical glucose sensor is coated with a porous hydrogel including a nanocatalyst, an oxidation-reduction reaction occurs when glucose, glucose oxidase, oxygen, and the nanocatalyst meet in the hydrogel, consequently, a change in glucose concentration may be wirelessly monitored in real time by measuring a current changed by electrons generated according to a result.

Specifically, glucose and oxygen in the body fluid comes into contact with flavin adenine dinucleotide (FAD), which is an oxidation-reduction reaction region in the glucose oxidase of the electrochemical glucose sensor, and thus an oxidation-reduction reaction in which hydrogen peroxide and gluconic acid are formed occurs. Thereafter, the hydrogen peroxide reacts with platinum on the surface of the nanocatalyst, and then rapidly decomposes into two electrons and two protons under a voltage in a range of 0.5 to 0.7V. In this case, a change in current occurs while the generated electrons flow from the working electrode to the counter electrode, and through this change, a change in glucose concentration may be measured.

The smart contact lens for diabetes diagnosis of the present disclosure is manufactured with materials having high biocompatibility, and thus may be safely applied to the body. For example, the smart contact lens for diabetes diagnosis of the present disclosure may be worn on a person's eye to wirelessly monitor the glucose concentration in real time.

Further, the present disclosure relates to a driving system including the above-described smart contact lens for diabetes diagnosis, and a wireless controller for driving the smart contact lens for diabetic diagnosis.

Figures 6A, 6B:
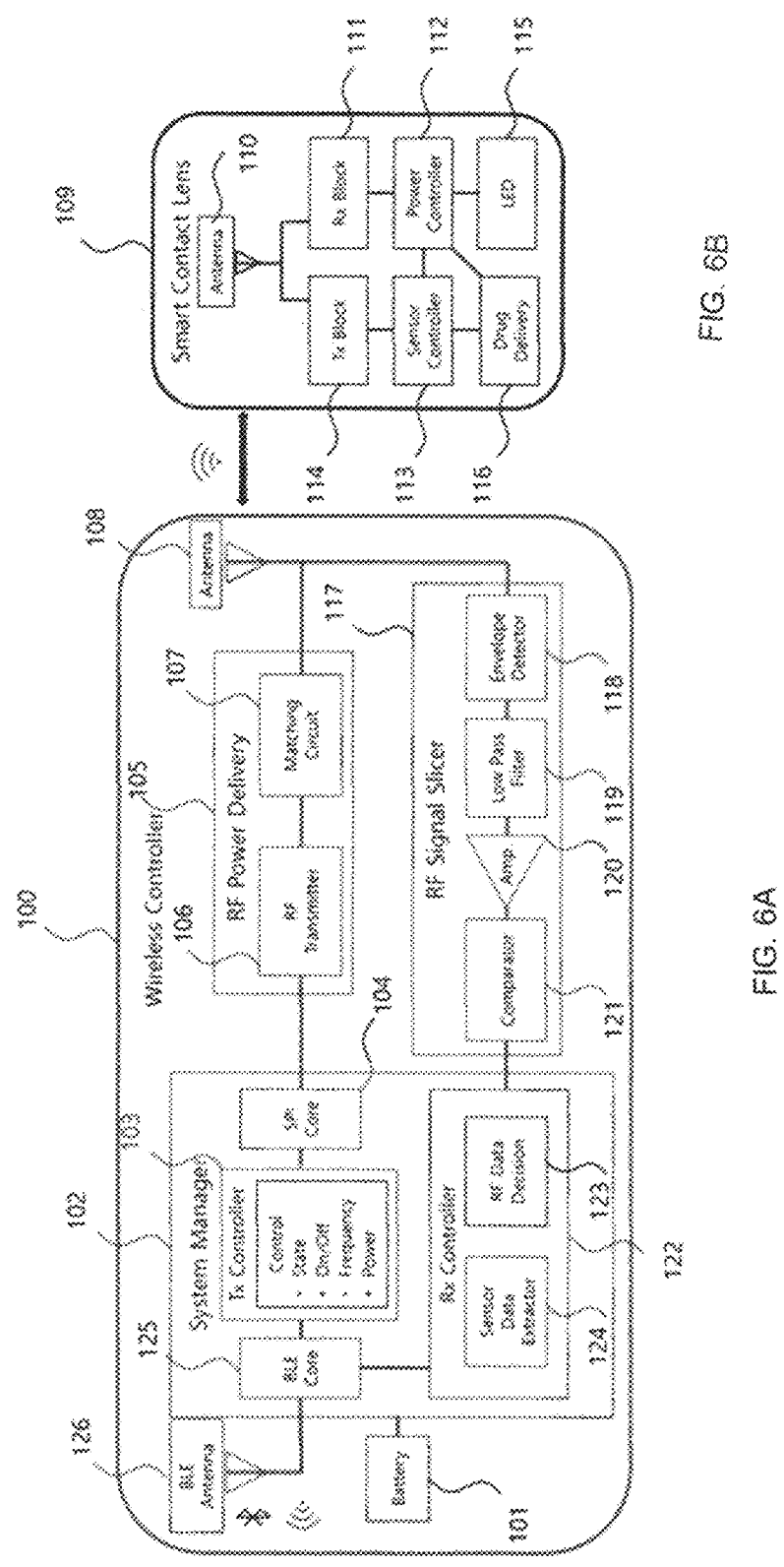
FIG. 6A illustrates a block diagram of a wireless controller according to the present disclosure and FIG. 6B illustrates a block diagram of the smart contact lens according to the present disclosure.
Figure 7A:
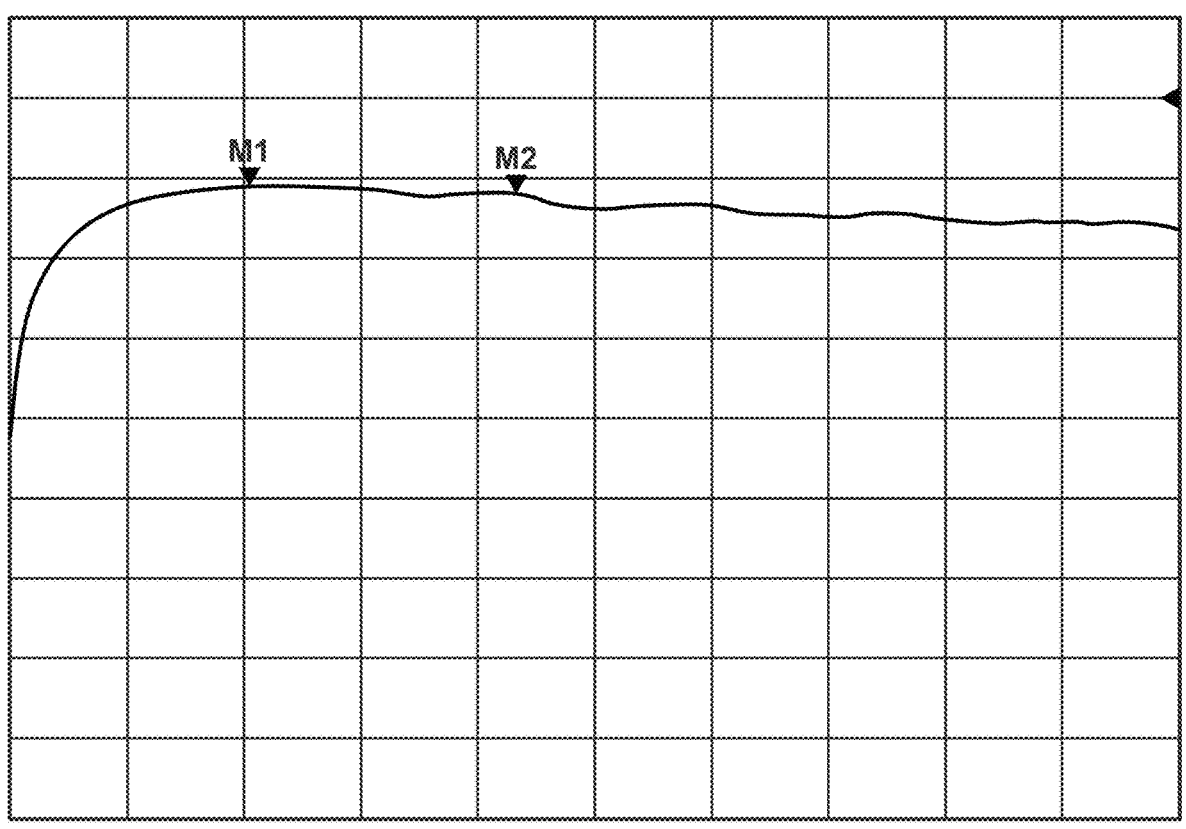
FIG. 7A illustrates simulation results for antennas of the wireless controller and the smart contact lens according to one embodiment of the present disclosure.
Figure 7B:
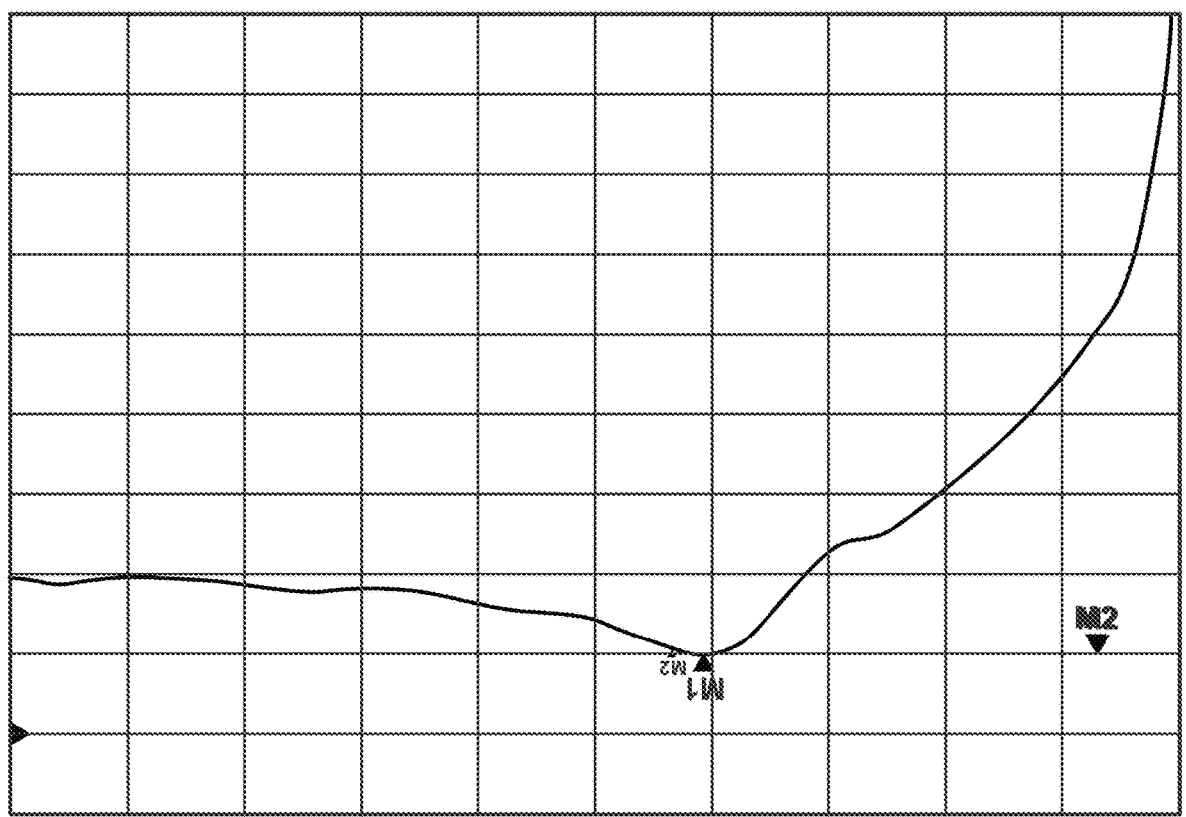
FIG. 7B illustrates simulation results for antennas of the wireless controller and the smart contact lens according to another embodiment of the present disclosure.
Figure 7C:
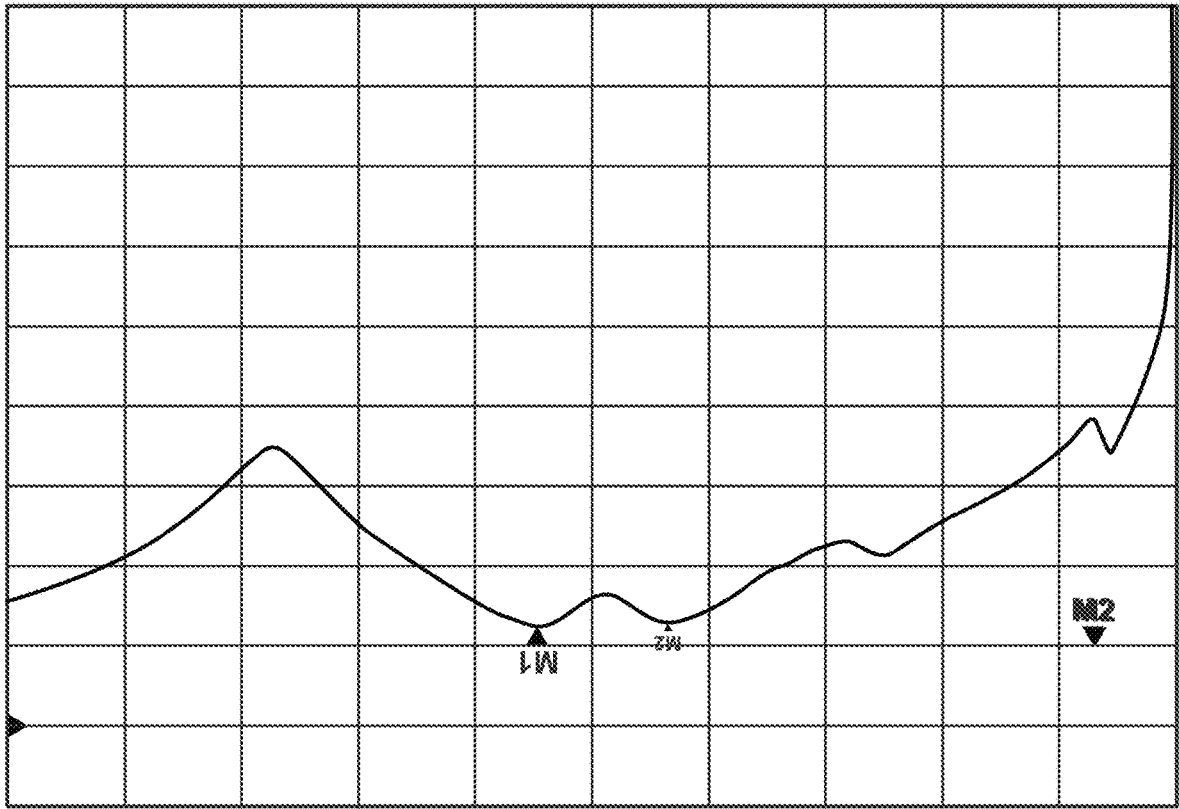
FIG. 7C illustrates simulation results for antennas of the wireless controller and the smart contact lens according to another embodiment of the present disclosure.
Figure 7D:
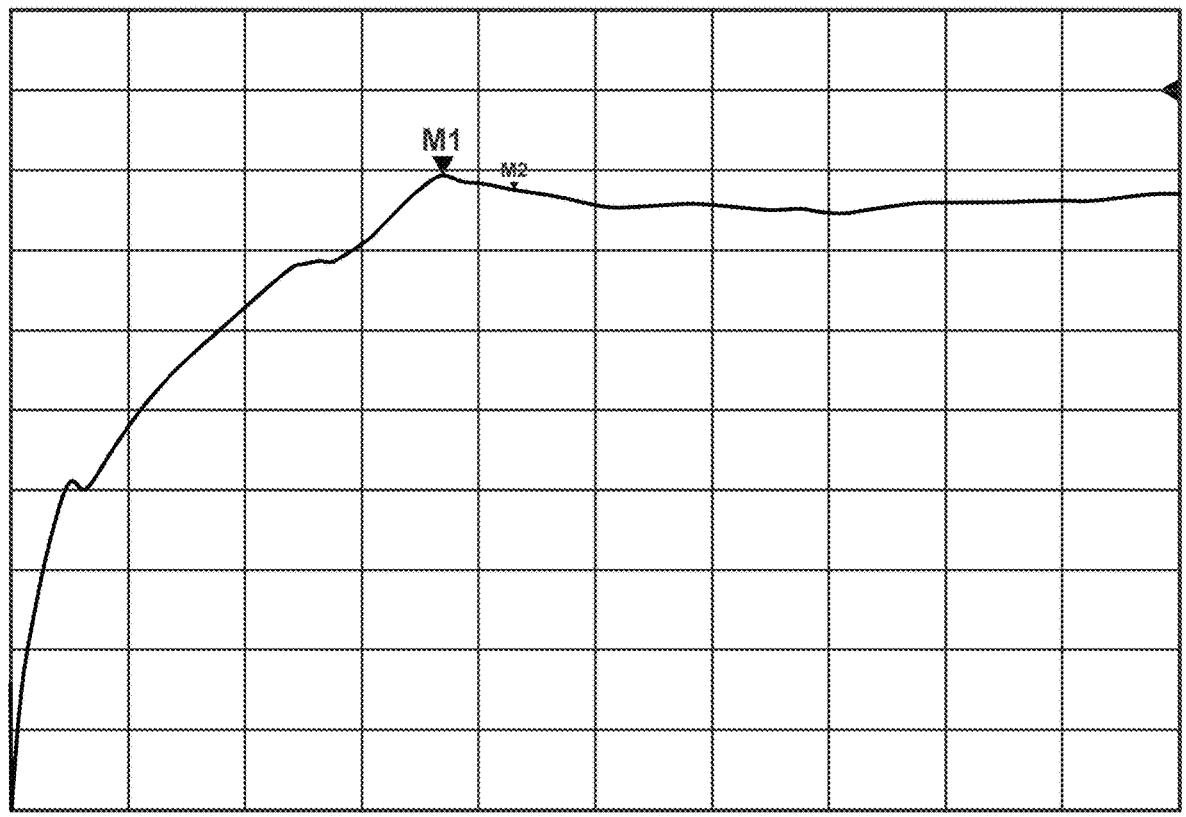
FIG. 7D illustrates simulation results for antennas of the wireless controller and the smart contact lens according to another embodiment of the present disclosure.

In the present disclosure, FIG. 6 illustrates a block diagram of the wireless controller and the smart contact lens. Hereinafter, the wireless controller and the driving system of the smart contact lens will be described in detail based on the block diagram.

In the present disclosure, a wireless controller 100 is composed of a power unit to which power is input, a battery unit 101 in which a battery is charged, a system manager 102 for controlling the entire device, a radio-frequency (RF) power transmission unit 105 for wireless power transmission, an antenna 108 and an RF signal discrimination unit 117 for sensing a sensor signal of the smart contact lens, and a Bluetooth antenna 126 for Bluetooth communication.

In the present disclosure, the battery may be charged in the battery unit 101.

The system manager 102 may be composed of a transmission controller (Tx controller) 103, a serial peripheral interface (SPI) core 104, a reception data processing unit (Rx Controller) 122, an RF data decision unit 123, a sensor data extractor 124, and a Bluetooth low energy (BLE) core 125. The RF power transmission unit 105 be composed of an RF transmitter 106 and an antenna matching circuit 107. Further, the RF signal discrimination unit 117 may include a detector 118, a low frequency filter 119, an amplifier 120, and a comparator 121.

In one embodiment, when the power of the battery unit 101 is connected, a command for power and frequency determined by the transmission controller 103 of the system manager 102 may be transmitted to the RF power transmission unit 105 through a connection of the SPI core 104.

The RF transmitter 106 of the RF power transmission unit 105 is connected to the antenna 108 through the antenna matching circuit 107 with the determined frequency and power, and the frequency and power may be transmitted to a smart contact lens 109.

In one embodiment, a sensor data signal transmitted from the smart contact lens 109 may be transmitted to the RF signal discrimination unit 117.

The detector 118 of the RF signal discrimination unit 117 may determine whether the signal is valid, and may remove power supply noise and the like after transmitting the signal to the low frequency filter 119. Thereafter, after the signal is amplified by the amplifier 120, the comparator 121 may determine the sensor data signal of the smart contact lens 109 and transmit the sensor data signal to the system manager 102.

In one embodiment, the data transmitted to the system manager 102 may finally be subjected to data validity determination in the RF data decision unit 123 of the received data processing unit 122, and required data may be transmitted to the BLE core 125 after being digitized in the sensor data extractor 124. Thereafter, the data may be transmitted to a smartphone through the Bluetooth antenna 126.

Figure 12C:
FIG. 12C schematically illustrates a wireless power and communication according to Experimental Example 4.
Figure 12D:
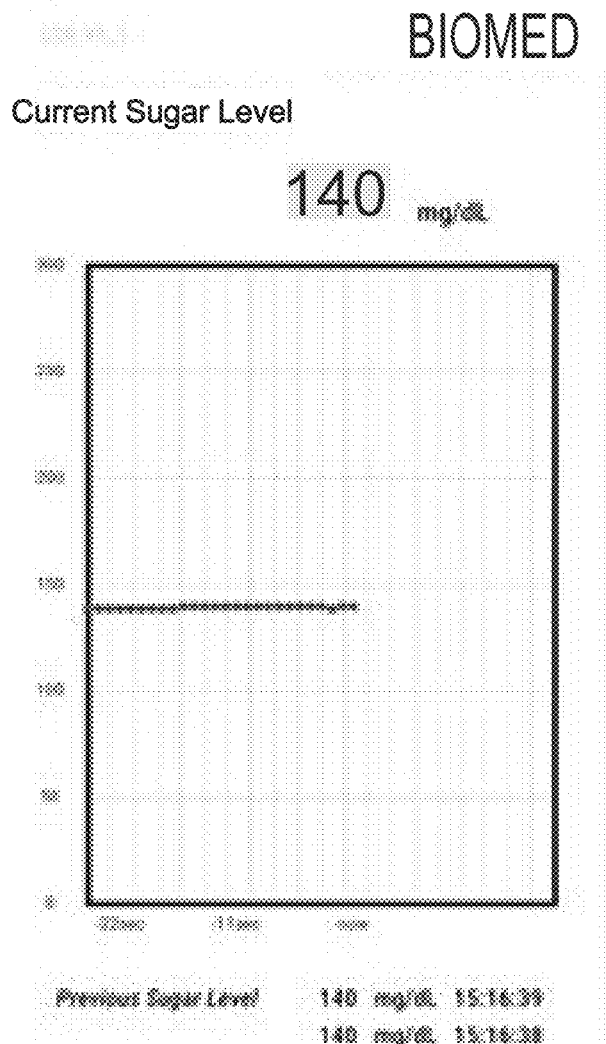
FIG. 12D illustrates glucose results obtained using the system discussed in Experimental Example 4.

In one embodiment, the sensor data transmitted to the smartphone is converted to an algorithm implemented through a sensor function and preliminary experiment data, and the converted data may be displayed on the smartphone (see FIG. 12).

In one embodiment, the antenna 108 of the wireless controller may emit a directional magnetic field when current is applied in a situation in which the antenna 110 of the smart contact lens 109 is disposed in parallel. For good power transmission, the antenna structure of the wireless controller may be configured based on simulation results based on a single loop antenna of the smart contact lens 109.

Specifically, the antenna 108 of the wireless controller 100 may be designed to have quantitative transmission efficiency according to the standard of the antenna 110 of the smart contact lens 109. Further, since the driving frequency of the wireless controller 100 is limited to the industry-science-medical (ISM) frequency band, the structure and size of the antenna 108 of the wireless controller may be designed based on the size and characteristics of the smart contact lens antenna 110.

In one embodiment, as the antenna 108 of the wireless controller uses an antenna manufactured with the same curvature and material as the antenna 110 of the contact lens to perform measurement of reflection loss and transmission loss, the antenna structure, thickness, and shape of the wireless controller may be optimized.

In one embodiment, the antenna 108 of the wireless controller is manufactured with the same curvature and material as the antenna 110 of the smart contact lens, and an optimum matching circuit of the two antennas may be configured using physiological saline, a printed circuit board, a plastic case, and the like.

The contact lens 109 of the present disclosure may be composed of an antenna 110 for power reception and data transmission, an RX block 111 for processing received power, a power controller 112 for supplying driving power to internal and external connection elements, a sensor controller 113 for controlling the sensor unit, a TX block 114 for sensor data communication, and a light-emitting diode (LED) 115, a drug delivery system 116, or the like according to a function of the contact lens.

In one embodiment, when the wireless power transmitted from the wireless controller 100 is transmitted to the antenna 110 of the smart contact lens 109, the RX block 111 may convert the received power with a detector and a rectifier, and transmit the converted power to the power controller 112. The signal detected by the sensor controller 113 may be converted through the TX block 114, and the data signal may be transmitted to the antenna 110 of the smart contact lens 109. The data signal may be transmitted to the antenna 108 of the wireless controller. The smart contact lens may drive an electronic device such as the LED 115, the drug delivery system 116, or the like according to the function thereof.

Hereinafter, the present disclosure is described in detail by the following examples. However, the following examples only exemplify the present disclosure, and the content of the present disclosure is not limited to the following examples.

EXAMPLES

In the present disclosure, FIG. 1 illustrates a board design diagram of the substrate of the smart contact lens for diabetes diagnosis according to the present disclosure.

In the present disclosure, the contact lens may be manufactured according to the drawing.

Manufacturing Example 1. Manufacture of Platinum-Plated Electrode

A platinum-plated electrode was manufactured on a colorless polyimide (CPI) film having a thickness of 12 μm.

Specifically, a Cu film of 3 to 5 μm was laminated on the CPI film to form a base electrode plate. After the base electrode plate was masked, a base electrode pattern was formed by treating the base electrode plate with an etching solution.

Thereafter, ruthenium and platinum were respectively plated to thicknesses of 50 to 100 nm and 100 to 500 nm using electroless electroplating. Accordingly, a platinum-plated electrode was formed.

Comparative-Manufacturing Example 1. Manufacture of Gold/Platinum Bimetallic Thin Film Electrode A bimetallic thin film electrode was manufactured on a polyethylene terephthalate (PET) film having a thickness of 23 μm.

Specifically, the PET film was sonicated with each of acetone and isopropyl alcohol (IPA) for 20 minutes. Thereafter, the PET film was dried with a nitrogen gun. It was deposited on a working electrode, a counter electrode, and a reference electrode at 220 nm/80 nm, 500 nm/15 nm, 500 nm/20 nm, and 500 nm/25 nm while changing the thickness of gold/platinum on the PET film using an electron beam evaporator.

In the present disclosure, FIGS. 2A and 2B are images of electrodes manufactured in Comparative-Manufacturing Example 1 and Manufacturing Example 1, respectively.

As shown in FIG. 2A, it can be seen that a mismatch portion where a lower electrode (Au) is exposed is generated in the electrode of Comparative-Manufacturing Example 1 manufactured in a vacuum deposition and photolithography method. This may adversely affect the stability of the electrode.

On the other hand, it can be seen that the electrode manufactured in Manufacturing Example 1 has excellent stability as the lower electrode can be completely shielded through a plating process.

Figure 3B:
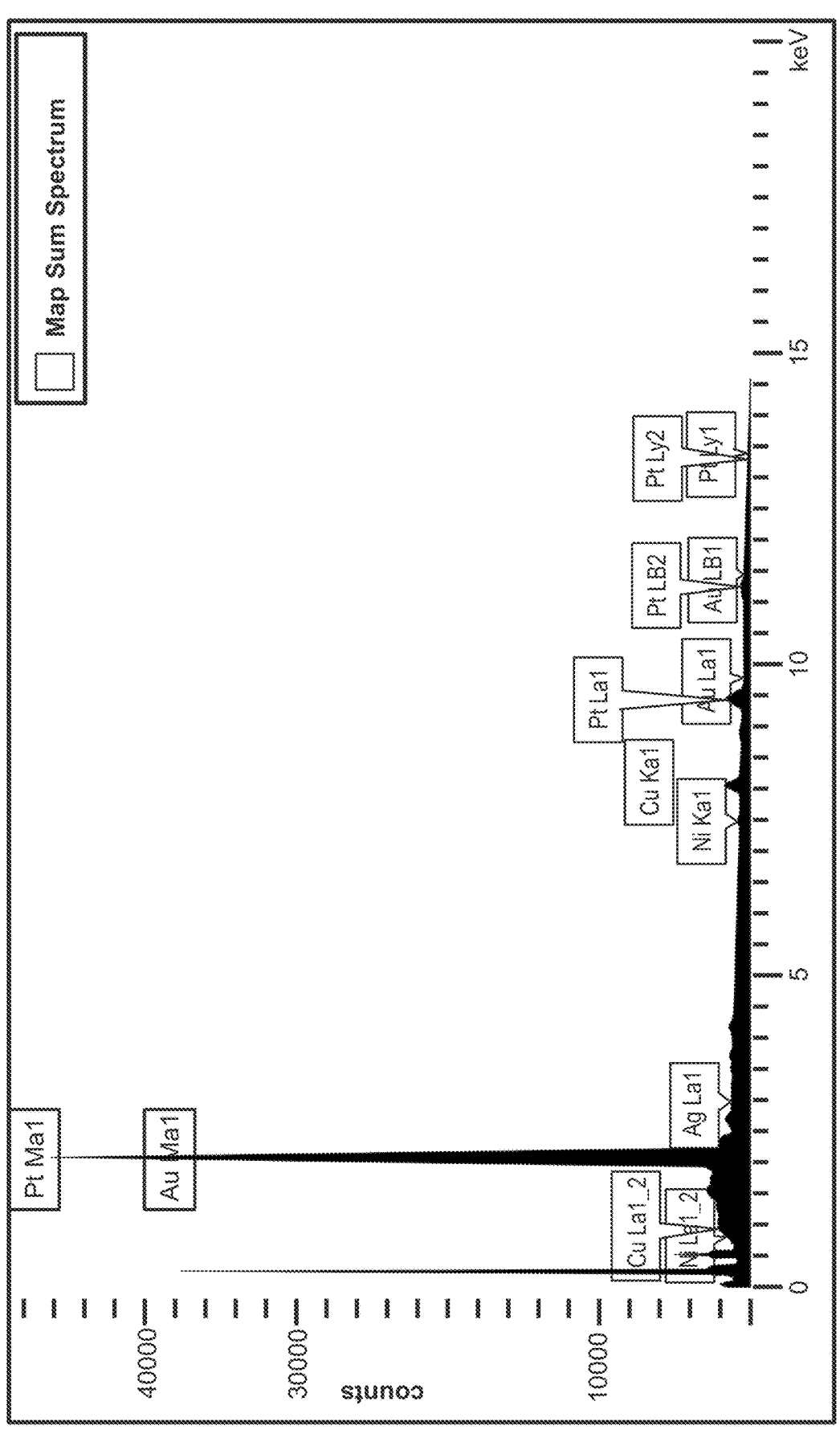
FIG. 3B is an energy dispersion spectroscopy analysis result of a platinum-plated electrode according to the present disclosure.

Further, in the present disclosure, FIG. 3 illustrates a scanning electron microscope image (FIG. 3A) and an energy dispersion spectroscopy analysis result (FIGS. 3B and 3C) of the platinum-plated electrode manufactured in Manufacturing Example 1.

As shown in FIG. 3, it can be seen that the surface of the platinum-plated electrode is formed with a platinum content of approximately 99%. Further, it can be seen that the lower electrode is not exposed even in a microelectrode pattern.

Manufacturing Example 2. Synthesis of Hyaluronic Acid Having Thiolated End and Hyaluronic Acid Having Thiolated Branch Hyaluronic acid having a thiolated end (end HA-SH) was synthesized by the reductive amination of hyaluronic acid with a diamine and a reducing agent.

Specifically, after dissolving 100 mg of hyaluronate (molecular weight: 10 kDa) and 120 mg of cystamine dihydrochloride in 20 ml of a borate buffer solution (0.1 M, pH 8.5), 0.4 M sodium chloride was additionally added and stirred for 2 hours in an incubator at 40° C. Subsequently, sodium cyanoborohydride (0.1 M) was added and incubated for 5 days at 40° C. Thereafter, DL-Dithiothreitol (DTT, 0.05 M) was added for 12 hours to reduce the disulfide bond of cystamine at an HA chain end. It was sequentially dialyzed against sodium hydroxide (0.3 M), 25% ethanol, and distilled water for 2 days, and then freeze-dried for 2 days. Accordingly, hyaluronic acid having a thiolated end was prepared.

After dissolving 100 mg of hyaluronic acid (HA molecular weight: 10, 100, or 200 kDa) in 20 ml of distilled water, (1-ethyl-3-(3-dimethylaminopropyl) carbodiimide (EDC) and N-hydroxysulfosuccinimide (sulfo-NHS) were respectively added at four and one times the mole ratio of HA. After adjusting the pH of the mixed solution to 5.5, the mixed solution was stirred for 30 minutes. Subsequently, cystamine dihydrochloride was added at four times the mole ratio of HA, and then stirred for one day. Thereafter, DTT (175 mM) was additionally added to adjust the pH of the solution to 8, and then stirred for 12 hours to reduce the disulfide bond of cystamine positioned at a branch of the HA. It was sequentially dialyzed against sodium hydroxide (0.3 M), 25% ethanol, and distilled water for 2 days, and then freeze-dried for 2 days. Accordingly, hyaluronic acid having a thiolated branch was prepared.

Manufacturing Example 3. Manufacture of Hyaluronic Acid-Platinum-Plated Electrode The platinum-plated electrode manufactured in Manufacturing Example 1 was immersed in 0.1 M sulfuric acid for one minute, and then washed with distilled water to wash the electrode surface.

A solution was prepared by dissolving each of the HA having a thiolated end (molecular weight: 10 kDa) and the HA having a thiolated branch (molecular weight: 10, 100, or 200 kDa) prepared in Manufacturing Example 2 in distilled water at a concentration of 2 mg/ml. The electrode was immersed in the solution for 24 hours to coat the surface of the electrode with the hyaluronic acid through a thiol-gold reaction. Thereafter, a hyaluronic acid-coated electrode (hyaluronic acid-platinum-plated electrode) was manufactured by washing the electrode three times with distilled water to remove unreacted HA, and drying the electrode in a vacuum desiccator.

Manufacturing Example 4. Manufacture of Electrochemical Glucose Sensor Including Hyaluronic Acid-Platinum-Plated Electrode The electrochemical sensor was manufactured on a CPI substrate having a thickness of 12 μm.

Specifically, a Cu film of 3 to 5 μm was laminated on the CPI film to form a base electrode plate. After the base electrode plate was masked, a base electrode pattern was formed by treating the base electrode plate with an etching solution. Thereafter, ruthenium and platinum were respectively plated to thicknesses of 50 to 100 nm and 100 to 500 nm to form a platinum-plated electrode using electroless electroplating.

A reference electrode (RE) was additionally formed with a silver/silver chloride (Ag/AgCl) paste on the electrode. Stability against physical and electrochemical damage was improved by covering a reaction region and a wire connection portion of three electrodes with a PDMS film, and then vapor-depositing (insulating) the remaining region with parylene C (500 nm).

Manufacturing Example 5. Synthesis of Hyaluronic Acid-Gold@Platinum Bimetallic Nanocatalyst HA-Au@Pt BiNCs were synthesized by a seed-mediated growth method.

First, gold nanoparticles (AuNPs) were synthesized as a seed to grow platinum on the surface of the AuNPs. Gold (III) chloride hydrate (2.5 ml of 4 mg/ml $HAuCl_4$) was mixed with deionized water (87.5 ml) and was heated to a boil with vigorous stirring. 5 ml of 25 mM sodium citrate was added to the boiling $HAuCl_4$ solution as a reducing agent for AuNPs synthesis and stirred until the color of the solution became like red wine. In order to remove aggregated particles, the AuNP solution was filtered with a 0.22 μm poly(vinylidene fluoride) (PVDF) syringe filter. The synthesized AuNP solution (3.77 nM) was used as a seed solution. Chloroplatinic acid ($H_2PtCl_6$, 1.504 ml, 0.1, 1, 4.5, or 10 mM) and L-ascorbic acid (0.1 M, 15.4 ml) were added to 20 ml of the AuNP seed solution. Thereafter, the mixed solution was vigorously stirred for 12 hours at room temperature. After removing the aggregated particles using the PVDF filter, the prepared Au@Pt solution (1.89 nM) was bonded to the gold surface and end HA-SH by gold-thiol bonding. Finally, the synthesized HA-Au@Pt BiNC solution was purified by centrifugation (10,000 g, 10 min) and redispersed in deionized (DI) water twice.

Manufacturing Example 6. Manufacture of Porous Hydrogel Including Bimetallic Nanocatalyst 10 mg/ml bovine serum albumin (BSA) was dissolved in a 2 wt % PVA solution in distilled water (to prepare a 10 mg/ml BSA solution), and 50 mg/ml GOx was dissolved in the 10 mg/ml BSA solution. Thereafter, a 0.5 wt % chitosan solution dissolved in 0.1 M acetic acid was mixed with the 50 mg/ml GOx in the same volume ratio. This solution was called a base solution.

To 40 μl of the base solution, magnesium particles (200 to 500 nm, 0 to 6 μl) and HA-Au@Pt BiNCs (18.9 nM, 30 μl) prepared in Manufacturing Example 5 were added and mixed. The solution including the magnesium particles and the HA-Au@Pt BiNCs was completely dried in a desiccator after drop casting 1 μl thereof.

A hydrogel was formed by crosslinking by drop casting 1 μl of 2 wt % glutaraldehyde on the coating. In order to form a nanoporous structure, the magnesium particles were removed by immersion in pH 5 PBS for 4 hours. The electrode was immersed in 1×PBS (pH: 7.4) for 24 hours to release an unreacted material, which is not crosslinked, from the hydrogel, and then washed with distilled water.

Manufacturing Example 7. Manufacture of Glucose Sensor to Which Porous Hydrogel Including Platinum-Plated Electrode and Nanocatalyst is Applied After connecting the electrochemical sensor manufactured in Manufacturing Example 4 to a wire using silver epoxy, a connection portion was coated with epoxy to block physical and chemical reactions. The working electrode was treated with UV ozone for 15 minutes to improve the hydrophilicity of an electrode surface and make a uniform coating.

Thereafter, as in Manufacturing Example 6, a reaction layer was formed by coating on a nanoporous hydrogel working electrode including a nanocatalyst.

Manufacturing Example 8. Manufacture of Smart Contact Lens

A pattern for flip-chip bonding of a platinum-plated electrode, an antenna, and an ASIC chip was formed using electroless electroplating on a CPI film (thickness: 12 μm).

Thereafter, a flip-chip bonding process was performed to connect the ASIC chip and the patterned platinum-plated electrode. In order to minimize the deformation of a shape of a substrate embedded in the smart contact lens, the remaining region of the substrate on which an electrochemical glucose sensor (platinum-plated electrode), the antenna, and the ASIC chip were integrated was cut with a press cutter to remove a film except for a patterned portion. An Ag/AgCl paste was applied to the reference electrode and then cured at 150° C. for 2 hours.

Stability of the electrode and the antenna against physical and chemical damage was improved by attaching a PDMS film having a thickness of 10 μm on the three electrodes and the antenna, and depositing parylene.

After mixing 10 g of a silicone elastomer (MED-6015, Avantor) and 1 g of a curing agent, air bubbles were removed in a vacuum desiccator. Thereafter, the air bubble free-silicone elastomer solution was immersed in a mold for manufacturing a lens. Before manufacturing the lens, the electrode treated with $O_2$ plasma (100 W, 5 minutes) was immersed in a lens manufacturing solution, and an upper mold was covered and crosslinked for 2 hours at 100° C. The manufactured contact lens was separated from the mold and ultrasonically washed with ethanol for 15 minutes.

The PDMS film was removed to expose the glucose sensor after opening the glucose sensor region with a circular punch. A porous hydrogel including a nanocatalyst was coated on the glucose sensor as in Manufacturing Example 6.

Figures 4A, 4B:
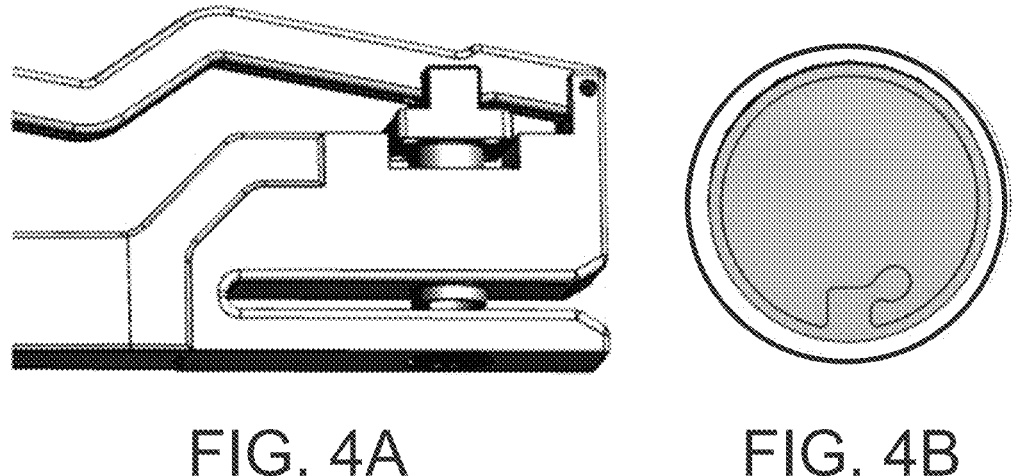
FIG. 4A illustrates an example of a press cutter for processing the platinum-plated electrode of the smart contact lens according to the present disclosure.
FIG. 4B illustrates the smart contact lens processed with a press cutter.

In the present disclosure, FIG. 4 illustrates the press cutter for processing the platinum-plated electrode of the smart contact lens.

As shown in FIG. 4, a portion other than an element and the electrode may be removed using the press cutter.

Since residual carbonized portions were generated when CPI was removed with a laser cutter, the CPI used as a flexible substrate could not be used as a substrate that is inserted into the contact lens. In the present disclosure, as the CPI is cut using the press cutter, the CPI may be applied to the contact lens.

Figure 5A:
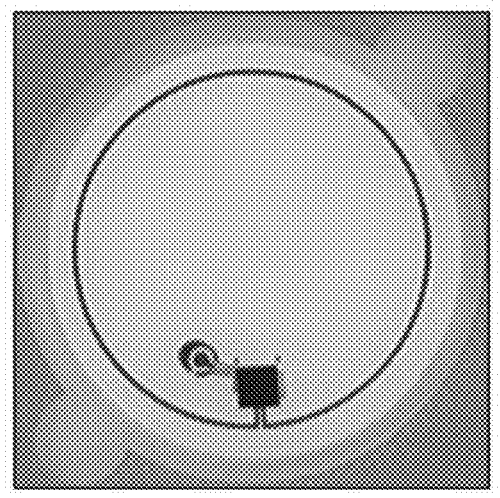
FIG. 5A illustrates a platinum-plated electrode substrate to which an application-specific integrated circuit (semiconductor) is bonded.
Figure 5B:
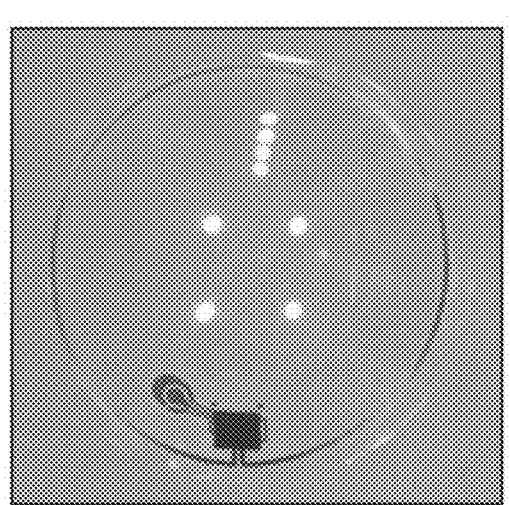
FIG. 5B illustrates a completed smart contact lens for diabetes diagnosis according to the present disclosure.

In the present disclosure, FIG. 5A illustrates the platinum-plated electrode substrate to which an application-specific integrated circuit is bonded according to the present disclosure, and FIG. 5B illustrates a completed smart contact lens.

The contact lens including the platinum-plated electrode may be manufactured through an embodiment of the present disclosure.

Manufacturing Example 9. Manufacture of Wireless Controller

A wireless controller having the block diagram configuration in FIG. 6 was manufactured.

Experimental Example 1. Simulation of Wireless Controller and Smart Contact Lens (1) Method A high frequency structure simulation software (HFSS, Ansys) simulation for various antennas introduced into the wireless controller and the smart contact lens were performed.

(2) Results

FIG. 7 illustrates simulation results for various antennas applied to the wireless controller and the smart contact lens. In the present Experimental Example, a simulation of various antennas of the wireless controller was performed based on the antenna of the smart contact lens.

The antenna of the wireless controller and the antenna of the smart contact lens used lens-type models having the same shape. In the present Experimental Example, a structure or thickness of the antenna may be optimized by connecting the two antennas with a coaxial cable and comparing the simulation results using a network analyzer or the like.

Thereafter, an optimum matching circuit of the two antennas may be configured after identifying characteristics of the two antennas using physiological saline, a printed circuit board, a plastic case, and the like.

In the present disclosure, when the wireless controller is placed on an eyeball in a state in which the smart contact lens is worn, real-time glucose measurement data may be monitored with a smartphone. Further, real-time treatment may be possible using an optical element, an electric element, a drug delivery system, and the like, which are linked with the sensor.

Figure 8:
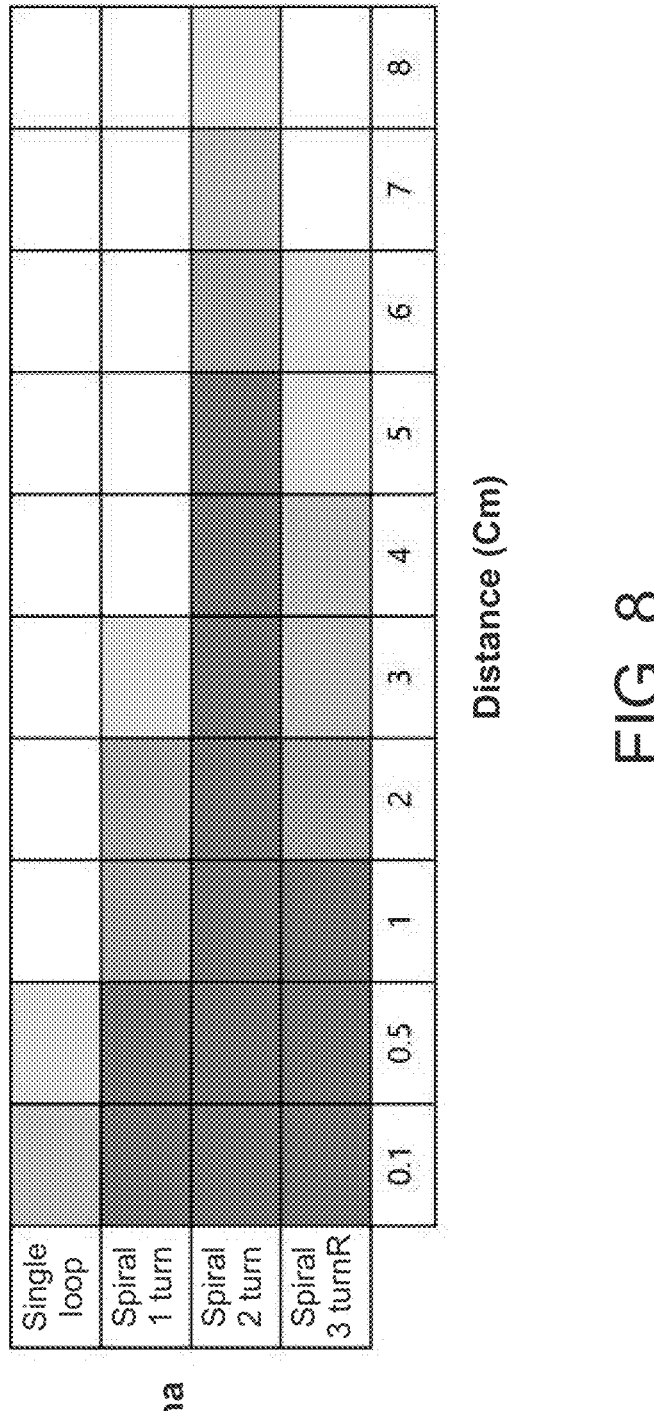
FIG. 8 illustrates wireless power transmission rates according to the types of antennas and the distance between the antennas applied to the wireless controller according to the present disclosure.

FIG. 8 illustrates wireless power transmission rates according to the types of antennas and the distance between the antennas applied to the wireless controller.

As a result of checking various power transmission rates for a single loop pattern antenna and one-, two-, and three-turn spiral antennas, it can be seen that power transmission is optimally driven in a two-turn spiral antenna pattern.

Figure 9:
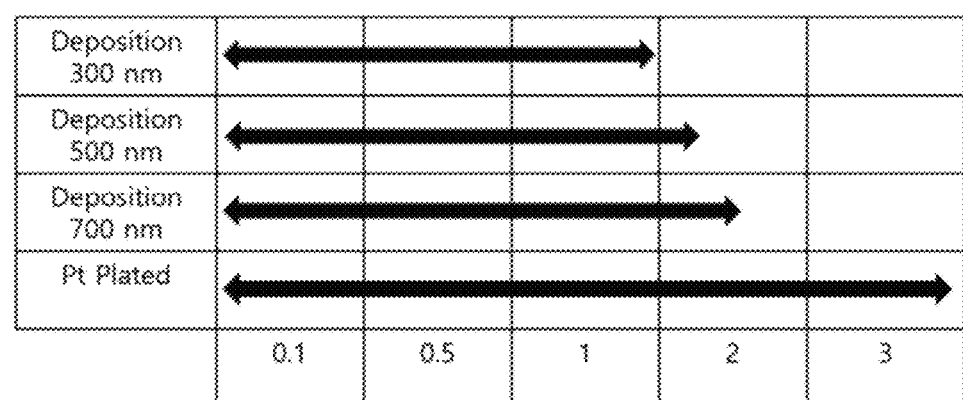
FIG. 9 illustrates a successful communication range according to the electrode condition and distance of the smart contact lens according to the present disclosure.

Further, FIG. 9 illustrates a successful communication range according to the electrode condition and distance of the smart contact lens.

As shown in FIG. 9, as a result of checking the range of a successful communication distance of the antenna of the smart contact lens under various deposition thickness conditions (300, 500, and 700 nm) of the antenna in the smart contact lens, it can be seen that the successful communication distance of the platinum-plated antenna (composed of 5 μm Cu/0.1 μm Ru/0.1 μm Pt) increases at least 2 to 3 times in the smart contact lens.

Experimental Example 2. Measurement of in Vitro Glucose Measurement Sensitivity of Smart Contact Lens (1) Method Sensitivity of the sensor into which the platinum-plated electrode of Manufacturing Example 1 was introduced and sensitivity of the electrochemical sensor into which the vacuum deposited electrode of Comparative-Manufacturing Example 1 was introduced were measured and compared. All experiments related to electrochemical performance were performed with a potentiostat (Ivium Tech. Co., AJ Eindhoven).

After filling a 50 ml beaker with 10 ml of PBS (0.1 M, pH 7.4), the three electrodes exposed for reaction were sufficiently immersed and each of the WE, RE, and CE was connected to the equipment (potentiostat). Thereafter, after adding a 10×3 mm stirring bar and putting the beaker on the stirrer, stirring was performed. After a voltage was applied (a voltage of 0.58 V was applied for 8 hours), a current was stabilized for 10 minutes, and the experiment was started when a base current was lowered to 50 nA or less.

After preparing 10,000 mg/dl, 1,000 mg/dl D-glucose solutions, each of 1, 4, 5, 10, 10, and 10 μL was slowly injected into a center of the beaker to gradually increase a glucose concentration to 1, 5, 10, 20, 30, and 40 mg/dL, and reacted for 40 minutes. A current value measured for each concentration was divided by an area of the working electrode, the current density was displayed on a graph, and after the current reached a maximum point, an average value was calculated with 30 data points. The sensitivity of the glucose sensor was calculated by dividing the current value calculated for each concentration by the concentration (units: mM). Sensitivity at a concentration of 0.1 mg/dl was used as a representative value.

(2) Results

Figure 10:
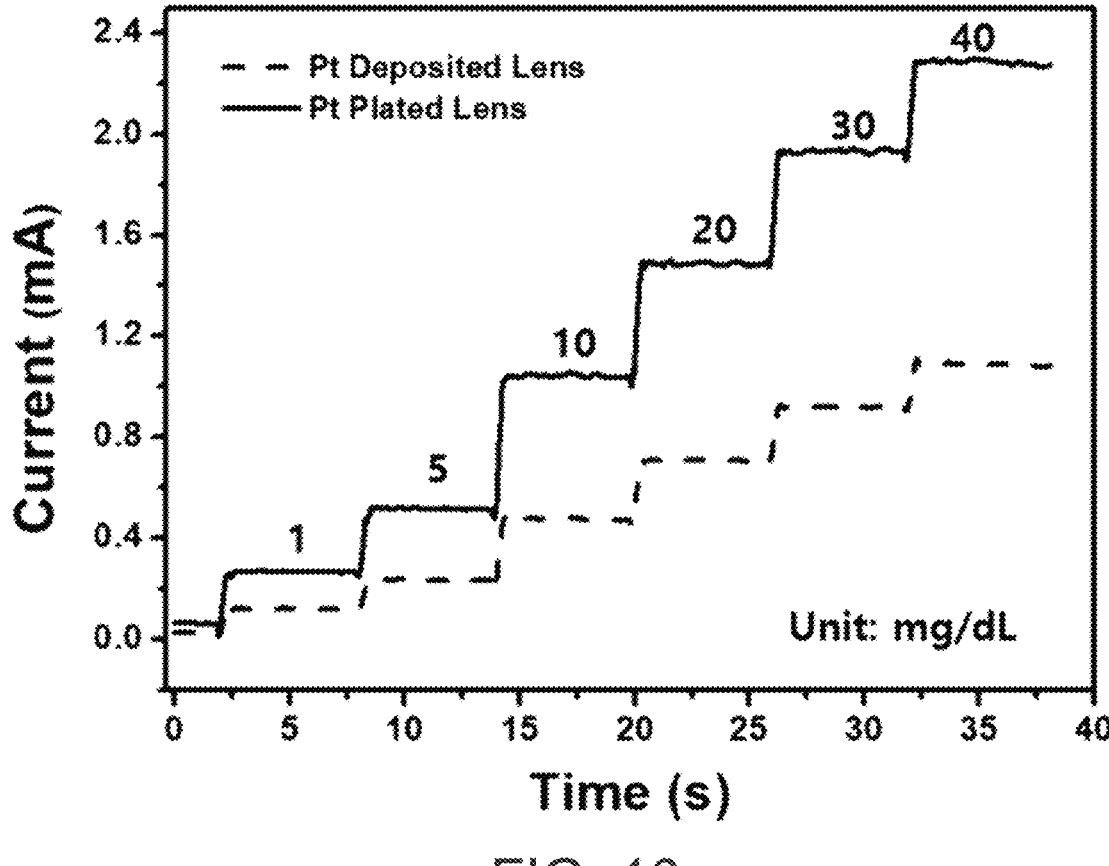
FIG. 10 illustrates the test results of in vitro glucose measurement sensitivity of the smart contact lens according to the present disclosure.

FIG. 10 illustrates the test results of in vitro glucose measurement sensitivity using the platinum-plated electrode according to the present disclosure.

As shown in FIG. 10, when the vacuum deposition method is used, it can be seen that low sensitivity is shown for all glucose concentrations.

When the platinum-plated electrode sensor according to the present disclosure is used, it can be seen that the platinum-plated electrode sensor has excellent sensitivity when applied to the diabetes diagnosis contact lens.

Experimental Example 3. Animal Model Preparation for Continuous Glucose Monitoring (1) Method All in vivo animal experiments were performed according to an Association for Research in Vision and Ophthalmology (ARVO) statement related to the use of animals in ophthalmic and vision research. The animal experiments were approved by the Institutional Animal Care and Use Committee (IACUC, KPC-M2020042) of the Korea Preclinical Center (KPC).

Alloxan (A7413, Sigma-Aldrich) was dissolved in PBS and then injected into New Zealand white rabbits (male, 2.8 to 3.8 kg, 15 to 17 weeks) at a concentration of 150 mg/kg. In order to prevent hypoglycemic shock, after fasting for 12 hours, alloxan was injected and 10% glucose was subcutaneously injected. A blood glucose level was measured with Accu-Chek Performa (Roche) on days three and seven after injection of alloxan. A commercially available continuous glucose monitoring system (CGM) was attached to the abdomen of a diabetic rabbit two hours before the experiment so that the rabbit has a warm-up time of two hours. Further, 0.8 ml of 10 mg/ml alfaxalone (Jurox) and rumpun (8:2 vol %) was injected into the diabetic rabbit ten minutes before the experiment. In order to artificially change the blood glucose level, 10 ml of 20% glucose and one unit of Humulin R were injected into the rabbit immediately before the experiment. After injection of 10 ml of 20% glucose in both diabetic and normal rabbits, blood glucose increased by approximately 10 to 15 mg/dl per 5 minutes, and after injection of one unit of Humulin R, blood glucose decreased by 5 to 10 mg/dl per 5 minutes. An in vivo test was performed on each rabbit for 45 minutes.

Figures 11A, 11B, 11C, 11D:
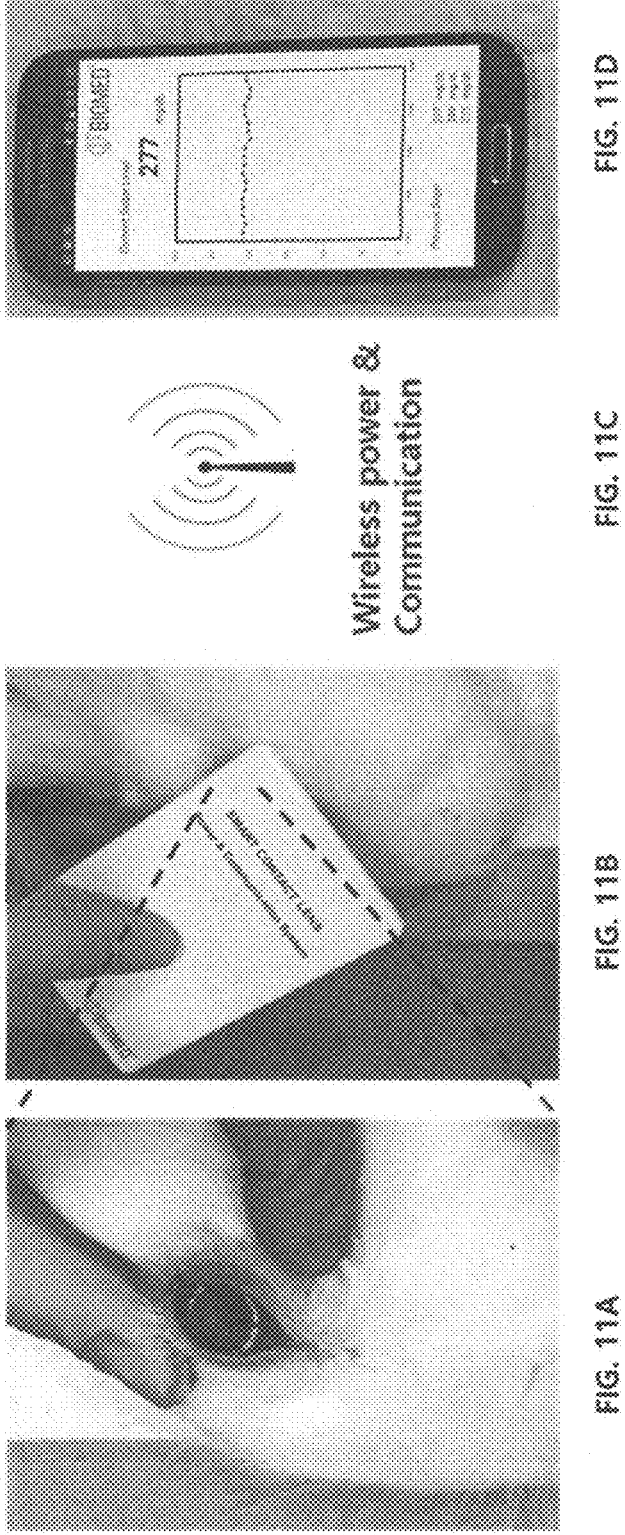
FIG. 11A illustrates a smart contact lens according to the present disclosure in a rabbit eye as explained in Experimental Example 3.
FIG. 11B shows a wireless controller according to the present disclosure held to the rabbit eye as explained in Experimental Example 3.
FIG. 11C schematically illustrates a wireless power and communication according to Experimental Example 3.
FIG. 11D illustrates glucose results obtained using the system discussed in Experimental Example 3.

FIG. 11 illustrates a glucose measurement example using the smart contact lens and the wireless controller.

The contact lens may be worn on a left eye (oculus sinister, OS) of each of the anesthetized diabetic and normal rabbits.

Experimental Example 4. Clinical Evaluation of Wireless Smart Contact Lens (1) Method A 41-year-old human subject wore a smart contact lens stored in a contact lens solution, and after aligning a flexible wireless board at a distance of 1 mm from an eye, a tear glucose level was measured with a smartphone application.

The smart contact lens was evaluated while strictly adhering to a protocol approved by the Pohang University of Science and Technology Bioethics Committee (POSTECH, PIRB-2021-A001). A digitized glucose sensor output was wirelessly transmitted through load modulation and was monitored on a smartphone through the same coil antenna.

(2) Results

FIG. 12 illustrates a photograph in which an actual person wears a smart contact lens for ultrasensitive diabetes diagnosis.

Wireless power transmission and data communication through inductive coupling between the smart contact lens of the human subject and an external reader can be demonstrated.

A platinum-plated electrode of the present disclosure is useful for mass production, and can prevent electrode damage and side effects due to ionic actions which can occur during an electrochemical reaction of a glucose sensor in tears or physiological saline. Accordingly, the stability of a smart contact lens can be greatly improved.

Further, in the present disclosure, when the platinum-plated electrode is manufactured, mass production can be easy and manufacturing time and manufacturing costs can be dramatically reduced by introducing a plating process instead of a general vacuum deposition method.

Since this plating process does not require photolithography, a masking process, and the like for electrode patterns during a metal deposition process, there is no pattern mismatch with a lower electrode layer, and the consistency and reliability of sensor operation due to step coverage can be greatly improved.

Further, since the platinum-plated electrode has high electrical conductivity, the wireless power transmission efficiency and data communication stability of the smart contact lens can be greatly improved. In addition, the sensitivity and reaction speed of the glucose sensor can be greatly increased through the high electrical conductivity.

In addition, the present disclosure provides a driving system using a smart contact lens for diabetes diagnosis and a wireless controller. The driving system is a system capable of monitoring a real-time glucose level with a smartphone, and can perform optical and drug treatment in conjunction with sensor data.

The driving system according to the present disclosure can be applied to treatment of metabolic diseases such as obesity and hypertension, and brain diseases such as Alzheimer's and Parkinson's diseases in addition to various eye diseases such as diabetes, glaucoma, diabetic retinopathy, dry eye syndrome, and the like. Further, the driving system can be used for driving and controlling the smart contact lens having a virtual or augmented reality display function with a built-in optical element.

In addition, in the present disclosure, an optimum antenna configuration for wireless driving of the smart contact lens can be provided. The wireless controller can monitor the sensor data of the smart contact lens in real time in conjunction with a smartphone and control sensor functions to control power. Further, the wireless controller can be used for good operation of a smart contact lens including a specific drug delivery system.

What is claimed is:

1. A smart contact lens for diabetes diagnosis, comprising:
a platinum-plated electrode including an electrically conductive layer and a reaction layer; and
a porous hydrogel including a nanocatalyst,
wherein the reaction layer includes platinum (Pt),
wherein the nanocatalyst comprises gold-platinum bimetallic nanoparticles with thiolated hyaluronic acid, and
wherein the porous hydrogel is prepared through:
preparing a base solution comprising polyvinyl alcohol (PVA), chitosan, bovine serum albumin (BSA), and glucose oxidase (GOx);
adding magnesium particles and the nanocatalyst to the base solution to prepare a mixture, drop casting and drying the mixture;
drop casting a solution comprising a glutaraldehyde and crosslinking the mixture; and
removing the magnesium particles.

2. The smart contact lens of claim 1, wherein the electrically conductive layer includes copper (Cu).

3. The smart contact lens of claim 1, wherein the platinum-plated electrode is used as one or more of a working electrode and a counter electrode.

4. The smart contact lens of claim 1, wherein:
the platinum-plated electrode is formed on a flexible substrate; and
the flexible substrate includes one or more selected from the group consisting of polyimide (PI), colorless PI (CPI), polyethylene naphthalate (PEN), and polycarbonate (PC).

5. The smart contact lens of claim 1, wherein:
the platinum-plated electrode is surface-treated with a first biocompatible polymer; and
the first biocompatible polymer includes one or more selected from the group consisting of polyethylene glycol, polylactic acid, polyglycolic acid, polylactic glycolic acid, polyvinylpyrrolidone, hyaluronic acid (HA) and a derivative thereof.

6. The smart contact lens of claim 1, wherein the platinum-plated electrode is manufactured through:
an operation of transferring an electrically conductive layer onto a flexible substrate;
an operation of plating an intermediate layer on the electrically conductive layer;
an operation of plating a reaction layer on the intermediate layer; and an operation of surface-treating the reaction layer with a first biocompatible polymer.

7. The smart contact lens of claim 1, wherein the porous hydrogel including the nanocatalyst is formed on a working electrode.

8. A driving system of a smart contact lens comprising:

the smart contact lens for diabetes diagnosis according to claim 1; and a wireless controller for driving the smart contact lens for diabetic diagnosis.

9. The driving system of claim 8, wherein the wireless controller (100) includes:

a power unit to which power is input;

a battery unit (101) in which a battery is charged;

a system manager (102) for controlling the entire device;

a radio-frequency (RF) power transmission unit (105) for wireless power transmission;

an antenna (108) and an RF signal discrimination unit (117) for sensing a sensor signal of the smart contact lens; and a Bluetooth antenna (126) for Bluetooth communication.

\* \* \* \* \*